United States Patent
Chavan et al.

(10) Patent No.: US 10,926,086 B2
(45) Date of Patent: Feb. 23, 2021

(54) LYMPHATIC SYSTEM NEUROMODULATION AND USES THEREOF

(71) Applicant: THE FEINSTEIN INSTITUTES FOR MEDICAL RESEARCH, Manhasset, NY (US)

(72) Inventors: Sangeeta S. Chavan, Syosset, NY (US); William M. Hanes, East Setauket, NY (US); Kevin J. Tracey, Old Greenwich, CT (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 167 days.

(21) Appl. No.: 16/075,161

(22) PCT Filed: Feb. 8, 2017

(86) PCT No.: PCT/US2017/016894
§ 371 (c)(1),
(2) Date: Aug. 3, 2018

(87) PCT Pub. No.: WO2017/142752
PCT Pub. Date: Aug. 24, 2017

(65) Prior Publication Data
US 2019/0038898 A1    Feb. 7, 2019

Related U.S. Application Data

(60) Provisional application No. 62/296,170, filed on Feb. 17, 2016.

(51) Int. Cl.
*A61N 1/32* (2006.01)
*A61N 1/36* (2006.01)
(Continued)

(52) U.S. Cl.
CPC .......... *A61N 1/36002* (2017.08); *A61K 41/00* (2013.01); *A61N 1/36017* (2013.01);
(Continued)

(58) Field of Classification Search
CPC ............ A61N 1/36002; A61N 1/36017; A61N 1/36146; A61N 1/36175; A61N 2/02;
(Continued)

(56) References Cited

U.S. PATENT DOCUMENTS 7,877,146 B2    1/2011  Rezai et al.
2005/0075701 A1*  4/2005  Shafer ................ A61N 1/36017
                                                                    607/72
(Continued)

OTHER PUBLICATIONS

PCT International Search Report and Written Opinion dated Apr. 20, 2017 in connection with PCT International Application No. PCT/US2017/016894, 9 pages.

*Primary Examiner* — Christine H Matthews
*Assistant Examiner* — Joshua Daryl D Lannu
(74) *Attorney, Agent, or Firm* — Amster, Rothstein & Ebenstein LLP

(57) ABSTRACT

Methods are disclosed for preventing systemic infection or controlling metastases or providing a vaccine adjuvant in a subject, the methods comprising stimulating one or more peripheral nerves innervating one or more lymph nodes of the subject.

12 Claims, 18 Drawing Sheets

(51) Int. Cl.
    *A61N 1/40*      (2006.01)
    *A61N 1/08*      (2006.01)
    *A61N 2/00*      (2006.01)
    *A61K 41/00*      (2020.01)
    *A61N 2/02*      (2006.01)
    *A61K 39/00*      (2006.01)
    *A61N 1/04*      (2006.01)

(52) U.S. Cl.
CPC ..... *A61N 1/36034* (2017.08); *A61N 1/36146* (2013.01); *A61N 1/36175* (2013.01); *A61N 2/006* (2013.01); *A61N 2/02* (2013.01); *A61K 39/00* (2013.01); *A61K 2039/575* (2013.01); *A61N 1/0456* (2013.01); *A61N 1/36171* (2013.01)

(58) Field of Classification Search
CPC .. A61N 2/006; A61N 1/0456; A61N 1/36171; A61N 1/36034; A61K 39/00; A61K 2039/575; A61K 41/00
See application file for complete search history.

(56) References Cited

U.S. PATENT DOCUMENTS

| | | |
|---|---|---|
| 2011/0150924 A1 | 6/2011 | Della Rocca et al. |
| 2011/0152967 A1* | 6/2011 | Simon ............... A61N 1/40 607/45 |

* cited by examiner

LYMPHATIC SYSTEM NEUROMODULATION AND USES THEREOF

CROSS-REFERENCE TO RELATED APPLICATIONS

This application is a U.S. national stage entry under 35 U.S.C. § 371 of PCT International Patent Application No. PCT/US2017/016894, filed Feb. 8, 2017, which claims the benefit of U.S. Provisional Patent Application No. 62/296,170, filed Feb. 17, 2016, the contents of which are incorporated herein by reference into the subject application.

STATEMENT OF GOVERNMENT SUPPORT

This invention was made with government support under grant number W911NF-09-1-0125 awarded by the Defense Advanced Research Projects Agency (DARPA). The government has certain rights in the invention.

BACKGROUND OF THE INVENTION

Throughout this application various publications are referred to in brackets. Full citations for these references may be found at the end of the specification. The disclosures of these publications are hereby incorporated by reference in their entirety into the subject application to more fully describe the art to which the subject invention pertains.

The lymphatic system is a series of lymph nodes arranged in a chain, connected by lymphatic vessels. Interstitial fluid from the tissue space drains into the end of these vessels and becomes lymph. This lymph carries substances from the tissue space, including pathogens, migrating immune cells, cancer cells from a drained tumor, together with fragments and molecules shed from any of these, to the lymph nodes where the immune system surveys this material. When a break in the epidermal layer of the skin occurs, bacteria can enter the soft tissue and the lymphatic system. Invading pathogens in lymph nodes are recognized by the host to initiate an immune response. Lymph eventually ascends into the thoracic duct where it enters the bloodstream through the subclavian vein.

Antigens from the skin drain into the lymphatics with lymph, or they are actively transported to the lymph node by dendritic cells after phagocytosis [1]. Soluble antigen traveling with the lymph to the lymph node is captured by antigen-presenting cells (APC) in the node, such as B cells and dendritic cells [2]. These cells line the system of reticular fibers that form conduits [3], which extend into the follicular regions and mediate delivery of small, soluble antigen [4]. APCs then degrade the pathogen and display fragments of antigen to T cells in the context of major-histocompatibility complex II (MHC II) on their surface membrane [5, 6], initiating an antigen-specific T cell activation [7]. T cells are activated by antigen in the context of MHC II, but B cells are able to recognize antigen in its native, unprocessed form via their B cell receptor (BCR), a surface-bound immunoglobulin (Ig) receptor [8]. This antigen-specific response is the basis for immunological memory, and allows for rapid response upon re-exposure to the same antigen.

In 1966-67, Nossal, Ada and their colleagues described changes in antigen localization in lymphatic tissue based on immunization status [9-11]. Following active or passive immunization, antigen is trapped in the lymph nodes draining the site of injection. If an animal is not immune to the antigen, it moves through the lymphatic system, from there entering the blood, liver, and spleen [9-11]. This phenomenon has been largely ignored, or at least uncited, since the initial description.

Lymph nodes are innervated by sympathetic and peptidergic neurons (reviewed in [12]). Tonkoff first described the presence of nerves in lymph nodes in 1899 [13]. In the 1980s, several groups utilized electron microscopy to confirm the presence of partially myelinated axons entering the node at the hilar region, as well as potential sensory nerve terminals branching into cortical and paracortical regions, terminating among T lymphocyte regions [14-18]. Immune cell responses might be modulated by the neurotransmitters released by these neurons [19-27]. Emerging data suggest a role for neurons in the detection of peripheral pathogenic bacteria and modulation of the subsequent immune response [28, 29]. Additionally, nerves can respond directly to antigen-antibody complexes through interaction with Fc receptors. Functional neuronal Fc receptors induce action potentials and calcium flux in response to antigen-antibody complexes [30-33], but their role in physiology remains unclear. These neuronal Fc receptors could underlie a mechanism in the detection of immunized antigen. Recent important work has focused on the specific cellular interactions with antigen within the individual lymph node [34-39].

Despite the important findings implicating nerve-regulation of lymphocyte cell trafficking [24, 27], whether nerves regulate antigen trafficking through the lymphatic system was unknown prior to studies disclosed herein, which show that sensory and motor nerves regulate antigen trafficking through distal to proximal lymph nodes.

The present invention addresses the need for improved methods for treating diseases and disorders, in particular methods that do not require administration of drugs to a subject. The methods disclosed herein use neuromodulation of the lymphatic system to elicit therapeutic responses.

SUMMARY OF THE INVENTION

Method are disclosed for preventing or inhibiting systemic infection or controlling metastases or providing a vaccine adjuvant in a subject, the methods comprising stimulating one or more peripheral nerves innervating one or more lymph nodes of the subject.

DETAILED DESCRIPTION OF THE INVENTION

Figure 1A:
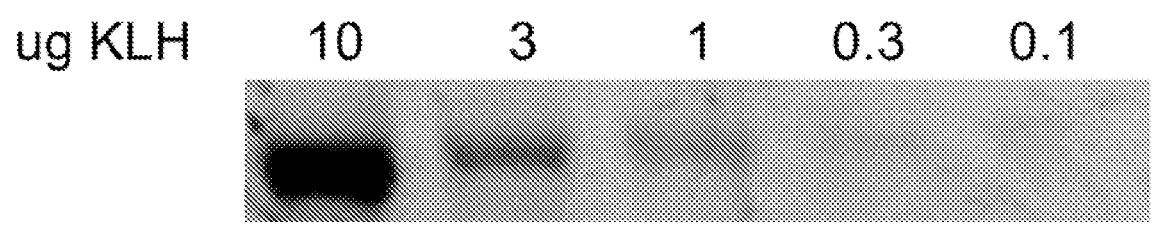
FIG. 1A-1G. Antigen flow through the lymphatic chain can be monitored with infrared fluorescent dye-labeled antigen. Keyhole limpet hemocyanin (KLH) was labeled with 800CW infrared fluorescent dye (KLH-800CW). A) Decreasing amounts of KLH-800CW were electrophoretically run on a polyacrylamide gel, then imaged on an Odyssey infrared imaging system. Image is a representative gel of two separate experiments. B) A linear correlation was found between amount of KLH-800CW and the measured fluorescent signal intensity. C-D) Indicated amounts of KLH-800CW were injected into the subcutaneous dorsum of the hind foot of Balb/c mice. When each whole mouse was imaged after one hour, larger amounts of injected KLH-800CW correlated with increased fluorescent signals located at both popliteal (C) and sciatic (D) lymph nodes, as well as the ratio of sciatic to popliteal signal, an approximation of antigen transfer. Bars represent means±SEM and n=5 measured fluorescence intensities for each injected concentration. A similar increase in signal was observed in E) popliteal and F) sciatic lymph nodes-isolated from mice injected with indicated amounts of KLH-800CW and minced into T-Per. Data represent means±SEM, n=5 per concentration. G) A linear correlation was found between in situ signal and in-plate signal with an R-squared value of 0.7634. The dotted line indicates the 95% prediction band.

The present invention provides a method of preventing systemic infection by infectious pathogens or controlling metastases or providing a vaccine adjuvant in a subject, the method comprising stimulating one or more peripheral nerves innervating one or more lymph nodes of the subject. Preferably, stimulation is applied in an amount and manner that is effective to reduce antigen flow through lymph nodes.

In one embodiment, stimulation is used to reduce or constrain infectious pathogens from traveling through the lymphatic system leading to systemic infection. Preferably, stimulation involves stimulating nerves innervating lymph nodes draining the site of an infection. For example, nerve stimulation can be applied after an injury to the skin of the subject, in particular after a large or deeply penetrating injury. Stimulation of nerves innervating lymph nodes draining the site of a penetrating injury to the subject can be used to prevent bacteremia and sepsis.

The infectious pathogen can be a virus, bacterium, prion, fungus, viroid and/or parasite. Commonly, the infectious pathogens include bacteria.

Cancers, especially carcinomas, can metastasize to new locations through the lymphatic system. Many therapeutic courses involve lymphatic mapping to determine the lymph nodes draining the site of a primary tumor. These lymph nodes are then monitored for development of new micrometastases. In one embodiment, stimulation can prevent tumor cells and micrometastases from traveling through the lymphatic system leading to a recolonization of cancer cells in a secondary tumor. Preferably, the stimulation involves stimulating nerves innervating lymph nodes draining the site of a primary tumor. Tumors are treated by surgical resection, chemotherapy, radiation, or a combination thereof. The present invention augments these therapies.

In a typical vaccination protocol, an antigen or a live or attenuated infectious agent is injected, usually in combination with an adjuvant to stimulate the immune system. Some patients fail to produce sufficient levels of immunoglobin in response to vaccination, and it can be difficult to obtain sufficient amounts of antigen for vaccination. In one embodiment, stimulation is used to increase antibody production to an antigen present in a vaccine. The present invention augments current vaccine techniques, and may require less antigen to obtain similar or higher titers of antibody.

In one embodiment, the femoral and sciatic nerves are stimulated in the popliteal fascia.

Electrical stimulation can be applied using, for example, a monopolar or bipolar needle electrode, a cluster of penetrating electrodes, percutaneous electrical nerve stimulation (PENS) (e.g., Biowave), transcutaneous electrical nerve stimulation (TENS) (e.g., truMedic), or an implanted nerve stimulator. Electrical nerve stimulation can be applied, for example, using 0.75 msec duration pulses at 2-20 Hz.

Magnetic nerve stimulation can be applied, for example, using an electromagnetic coil creating a time-variable magnetic field (e.g., MagVenture coils).

Electrical or magnetic stimulation can be applied, for example, for a duration of at least 1 minute. One or more sessions of electrical or magnetic stimulation can be used.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Neuronal Circuits Modulate Flow Through Lymph Nodes

Overview

After a break in the skin, bacteria can enter the tissues, eventually passing through the lymphatic system and into the bloodstream leading to systemic spread of infection. Bacteria and antigens in immunized animals become trapped in the initial lymph nodes, but the mechanisms that control this phenomenon are poorly understood. This Example describes a role for neurons in sensing and restricting flow of antigens from node to node in the lymphatic system. Antigen injected into the dorsum of the mouse hind foot travels first to the popliteal lymph node, then sequentially to the sciatic lymph node, continuing through the lymphatics to eventually reach the blood stream. Following immunization to Keyhole-Limpet Hemocyanin (KLH), the flow of IrDye-labeled KLH in mice was restricted through the popliteal and sciatic lymph nodes. Imaging one hour after antigen administration revealed a significant decrease in the transfer of antigen from the popliteal to the sciatic lymph node in immunized mice as compared to naïve animals (naïve 54.34±8.840 versus immunized 9.730±3.715, $p<0.001$). Blocking neuronal activity with bupivacaine at the lymph nodes of immunized animals at the time of challenge with labeled antigen resulted in restoration of inter-nodal antigen transport, with a corresponding increase in antigen signal (saline 31.45±3.759 versus bupivacaine 45.65±5.350, $p<0.05$). A loss of restriction of antigen transfer was observed in animals with NaV1.8-depleted sensory neuron populations (control 15.41±3.526 versus NaV1.8-DTA 35.56±6.035, $p<0.05$). Conversely, direct activation of neuronal signals by noninvasive magnetic stimulation resulted in a significant decrease of antigen trafficking as compared to sham controls (sham stimulated 55.99±4.993 versus magnetically stimulated 30.87±4.169, $p<0.001$). Skin samples taken from the injection site of immunized animals showed colocalization of PGP9.5-expressing neurons, FcγRI receptors and antigen. Additionally, animals with a FcγRI/FcεRI knockout phenotype fail to restrict antigen transfer. Taken together, these studies reveal a novel neuronal circuit that modulates antigen trafficking in the lymphatic system, wherein the neuronal substrate of the circuit involves antigen interaction with Fc receptors.

Materials and Methods

Animals. Balb/c, B6.129P2-Gt(ROSA)26Sor$^{tm1(DTA)Lky}$ (floxed-stop-DTA, "DTA"), B6.129-Trpv1$^{tm1(cre)Bbm}$ (TRPV1-cre), and B6;129P2-Fcer1g$^{tm1Rav}$ (FcR KO) mice were obtained from Jackson Laboratories. FcR KO mice lack the Fcγ adaptor protein, which transduces FcγRI and FcεRI signaling. Nav1.8-Cre [40] mice were a gift to Dr. Woolf from R. Kuner (University of Heidelberg). Nav1.8-Cre$^{+/-}$ mice were bred with C57BL/6 DTA$^{+/+}$ mice to generate nociceptor-deficient Nav1.8-Cre$^{+/-}$/DTA$^{+/-}$ and control littermates (Nav1.8-Cre$^{-/-}$/DTA$^{+/-}$). TRPV1-Cre$^{+/-}$ mice were bred with C57BL/6 DTA$^{+/+}$ mice to generate TRPV1-Cre$^{+/-}$/DTA$^{+/-}$ and control littermates (TRPV1-Cre$^{-/-}$/DTA$^{+/-}$). Food and water were available ad libitum. Mice were used in subsequent experiments after at least a 14-day-adaptation period. All procedures were performed in accordance with the National Institutes of Health (NIH) Guidelines [41] under protocols approved by the Institutional Animal Care and Use Committee (IACUC) of the Feinstein Institute for Medical Research.

Antigen labeling. Keyhole limpet hemocyanin (KLH, Calbiochem) or ovalbumin (OVA, Sigma-Aldrich) were diluted to 1 mg/mL with phosphate-buffered saline (PBS), then potassium phosphate, dibasic, pH 9.0 was added to 0.1M final concentration. 0.5 mg IrDye (800CW-NHS ester or 680LT-NHS ester, Licor) or Alexa Fluor® 647 NHS Ester (A647, Thermo Scientific) was added for each 25 mg protein. 1 mL aliquots were incubated at 20° C. with 300 RPM shaking for 2 hours. Free label was separated by centrifugation through PBS-washed Zeba spin desalting columns (Thermo Scientific). Dye-labeled antigens were concentrated with 100K (KLH) or 30K MWCO (OVA) spin columns (Millipore).

Gel Electrophoresis. Labeled antigens were loaded on NuPAGE 4-12% Bis-Tris Gels (Invitrogen) with NuPAGE MOPS SDS Running Buffer and run according to manufacturer's instructions, 50 minutes at 200 constant volts. Gels were extracted from cassettes and imaged directly on an Odyssey infrared imager (Licor).

In situ Antigen Imaging. 20 μl of 100 μg/ml labeled antigen was injected subcutaneously into the dorsum of the hind paw with an insulin syringe. After the predetermined time, the animal was euthanized using carbon dioxide, the skin over the area of interest was removed, and the animal was placed in a supine position in an Odyssey infrared imager. To image lymph node antigen content, sciatic and popliteal lymph nodes were surgically removed and placed into black, clear-bottomed 96-well plates filled with T-per (Thermo Scientific). These plates were imaged on the Odyssey imager.

Immunization. Unlabeled antigen (100 μg) and 50% Imject alum (Thermo Scientific) in 200 μl 0.9% saline was injected intraperitoneally. Two weeks later, animals were injected again with the same solution as a booster. Two weeks after the booster injection, animals were used for experiments. Control animals received injections of 50% alum in saline.

Antigen-specific Antibody Titer. High-binding 96-well microplates (Corning) were coated using 20 μg/mL KLH in phosphate-buffered saline (PBS), and incubated overnight at room temperature. The following day, the plates were washed with PBS+0.01% Tween20 and blocked with 1 mg/mL bovine serum albumin in PBS. Serum from immunized animals was obtained by cardiac puncture followed by centrifugation at 2,000×g for 10 minutes. Serum was diluted 1:100-1:10,000 with PBS and 100 μl per sample added to washed and blocked plates. Plates were incubated for 2 hours followed by incubation with 1:2000 sheep-derived anti-mouse IgM-HRP (BD) or anti-mouse IgG (Amersham) for 2 hours. Plates were washed a final time, developed using Opt-EIA (BD), and the reaction stopped with $H_2SO_4$.

Nerve Block. Mice were immunized with 100 μg antigen and 50% Imject alum in 200 μl saline injected intraperitoneally twice, two weeks apart. Two weeks after the second injections, 25 μl bupivacaine (0.375%, APP Pharmaceuticals) or 0.9% saline was injected at the sciatic nerve and the femoral nerve of the hind leg. 20 minutes after the initial injection, animals were injected with labeled antigen in the dorsum of the hind paw. After one hour, animals were euthanized and imaged.

Electrical nerve stimulation. Mice were anesthetized using isoflurane in a prone position. A 28 gauge, uncoated grounding electrode (Technomed) was placed subcutaneously at the top of the thigh, and a coated needle electrode (Alpine Biomed) was inserted adjacent to the popliteal lymph node. Stimulation delivered by a Biopac stimulation module controlled with AcqKnowledge 4.1 software. Parameters were −5V constant, 0.75 msec pulse duration, 20 Hz (50 msec period). Stimulation was applied for five minutes; after the first minute, KLH-800CW was injected into the dorsum of the hind paw. Mice were allowed to awaken, then euthanized and imaged after one hour.

Magnetic Nerve Stimulation. Mice were anesthetized using isoflurane in a prone position. Magnetic stimulation administered using an MC-B35 butterfly coil driven by a MagPro stimulator (Magventure) focused the popliteal and sciatic lymph nodes. The parameters used were: 50% power, 120 pulses (2 Hz, 60 s) train 1, 1 s train interval. Control animals were anesthetized and the magnetic coil was positioned, but no current applied. Immediately after stimulation, mice were removed from the table, then KLH-800CW was injected into the dorsum of the hind paw. Mice were allowed to awaken, then euthanized and imaged after one hour.

Passive Immunization. Naïve Balb/c mice were injected intraperitoneally with 100 μg rabbit polyclonal anti-ovalbumin antibody (Millipore). After 24 hours, mice were injected with OVA-800CW or KLH-800CW subcutaneously in the dorsum of the hind paw. After one hour, mice were euthanized and imaged.

Tissue staining. Mice were immunized with 100 μg antigen and 50% Imject alum in 200 μl saline injected intraperitoneally twice, two weeks apart. Two weeks after the second injection, mice were injected with KLH-A647 in the dorsum of the hind paw. After one hour, skin around the injection site was excised, frozen in optimal cutting temperature (OCT) media (Tissue-Tek), sliced at 10 μm, and mounted on Superfrost/Plus slides (Fisher Scientific). Sections were blocked with 5% goat serum, and rat anti-CD16/CD32 (BD Biosciences). Sections were then stained for 1 hour with rabbit anti-PGP9.5 (EMD Millipore) and mouse anti-CD64 (Biolegend, clone X54-5/7.1). Secondary antibodies were goat anti-mouse IgG-Dylight 550 and goat anti-rabbit IgG-Dylight 488 (Thermo Scientific). Images were obtained on a FluoView FV300 laser-scanning confocal microscope (Olympus).

Statistics. Antigen concentration compared to fluorescence and in situ compared to in plate fluorescence were analyzed by linear regression. Control and experimental popliteal and sciatic lymph node signals were individually analyzed by unpaired student's t-test. Antigen concentration curves and Control/TRPV1/$Na_V1.8$ lymph node fluorescence were analyzed by one-way ANOVA followed by Bonferroni post-test. All tests with a P value of less than 0.05 were considered statistically significant. Statistical analyses were performed using Graphpad Prism 6 software. Unless otherwise stated, all numbers are given as average±standard error of the mean. 'n' represents the number of mice used in each group. In graphs, "*" indicates p<0.05, "" indicates p<0.01, "*" indicates p<0.001, and "****" indicates p<0.0001.

Results

Figure 1B:
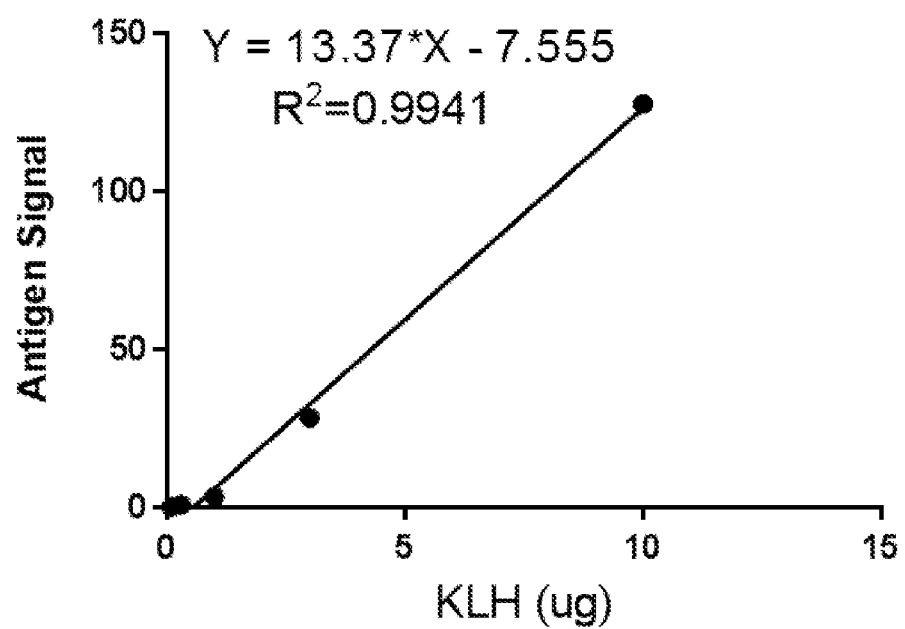
Figure 1C:
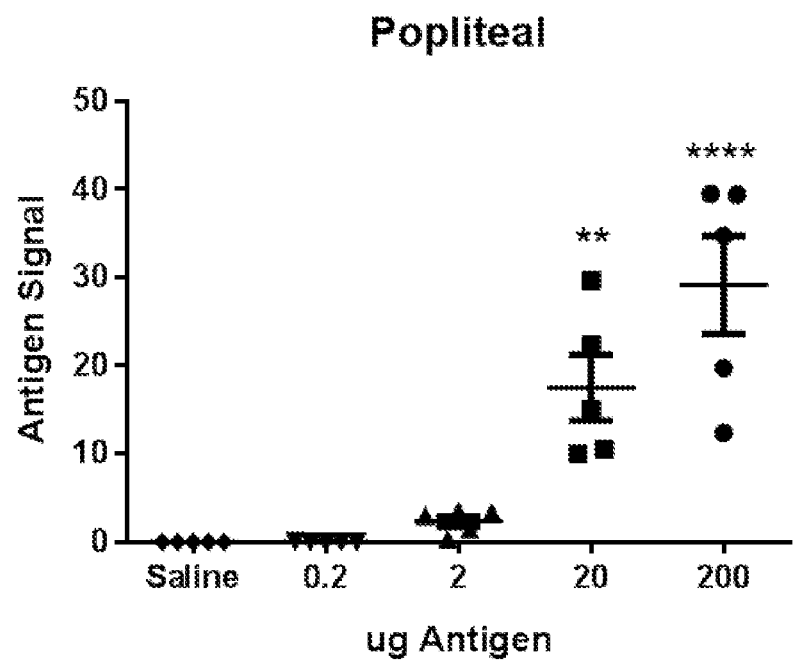
Figure 1D:
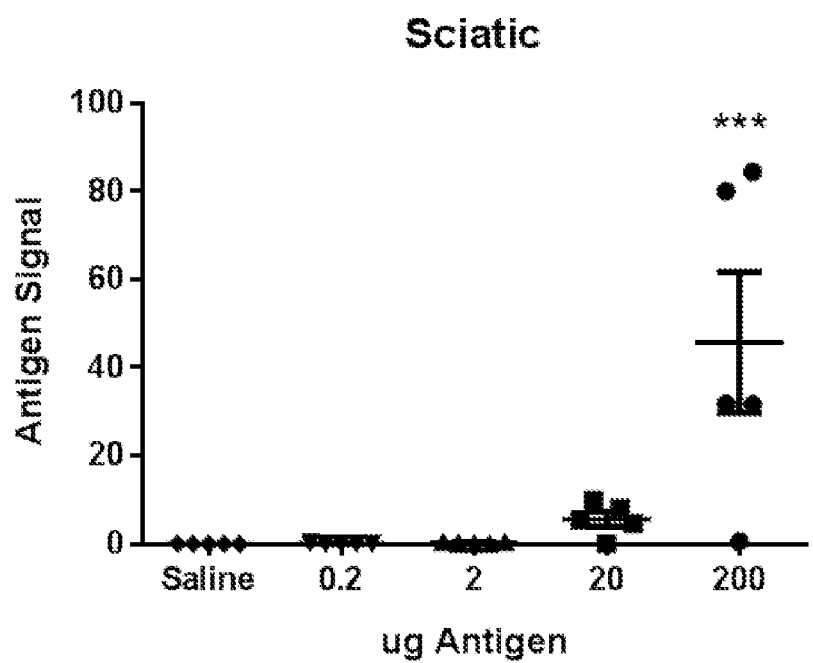
Figure 1E:
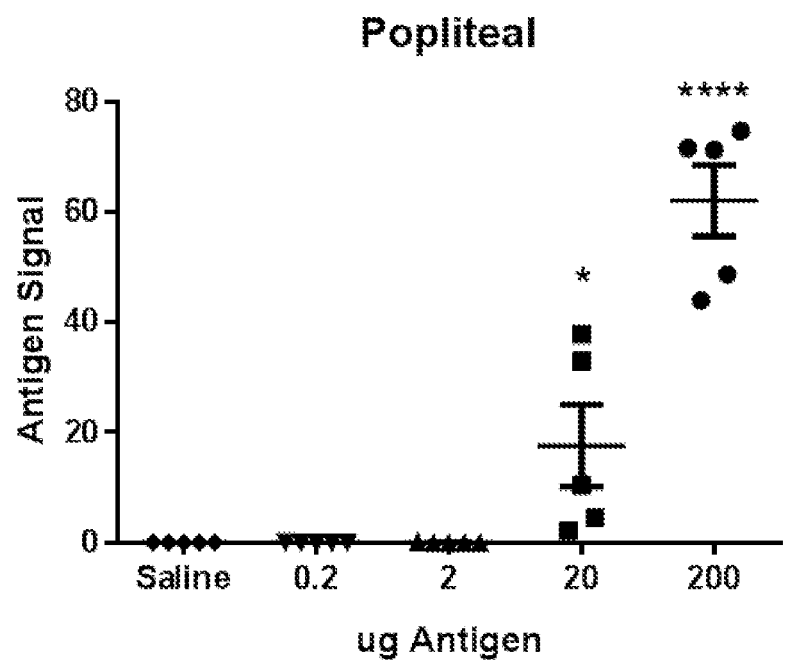
Figure 1F:
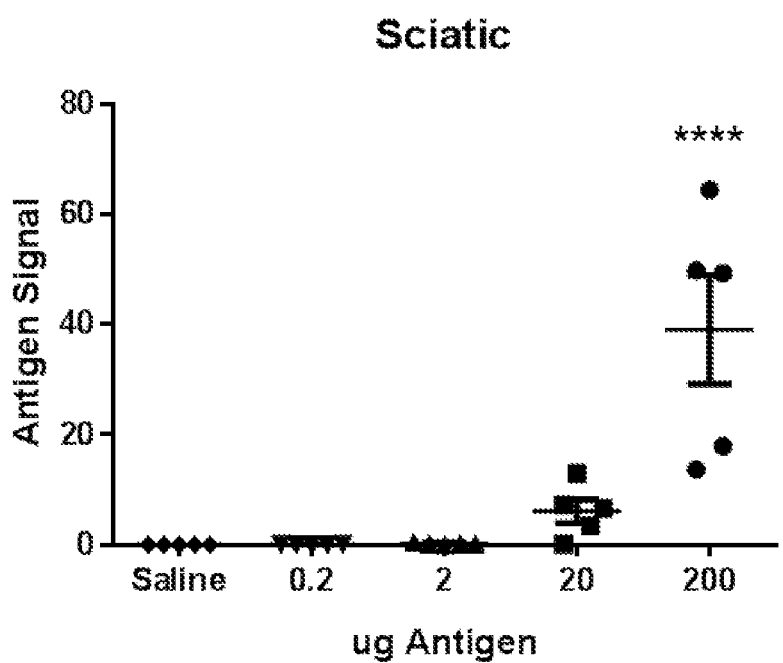
Figure 1G:
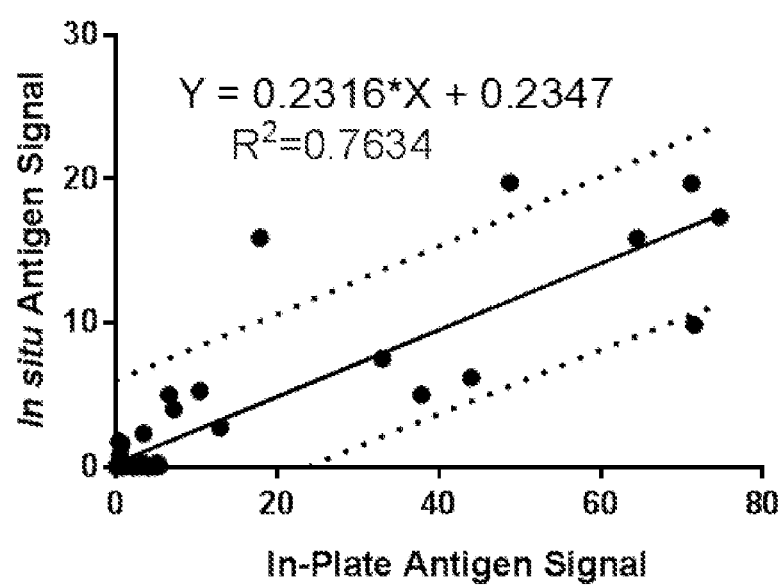

Antigen flow through the lymphatic chain can be monitored with infrared fluorescent dye-labeled antigen. Antigens linked to near infrared fluorescent dyes were used to monitor antigen localization and concentration in the peripheral lymphatic tissue. This allowed imaging of whole animals using a Licor Odyssey flatbed imager with low background and relatively high resolution, in situ, giving a view of the involved lymphatic system as a whole. To validate this method, various concentrations of dye-labeled antigen were electrophoresed in a polyacrylamide gel to concentrate known amounts in localized bands. After imaging the gel on a Licor Odyssey infrared plate imager, a linear correlation between antigen concentration and fluorescent signal was found (FIGS. 1A and 1B). When a range of concentrations of labeled antigen was injected in the dorsum of the hind paw of a mouse, a dose-dependent fluorescent signal could be detected from the foot (not shown), to the popliteal lymph node (FIG. 1C), to the sciatic lymph node (FIG. 1D), then up the rest of the chain of lymph nodes (not shown). When the popliteal and sciatic lymph nodes were then isolated and imaged in a 96-well plate, a similar dose-dependent fluorescent signal was observed in the popliteal (FIG. 1E) and sciatic lymph nodes (FIG. 1F). A linear correlation with an R-squared value of 0.7634 was found when plotting the in situ fluorescent signal against the signal in the 96-well plate (FIG. 1G). These data indicate that fluorescently labeled antigen can be used to monitor the localization and concentration of antigen appearing in the lymphatic system that drains sites of subcutaneously administered antigen in the distal hindlimb.

Figure 2A:
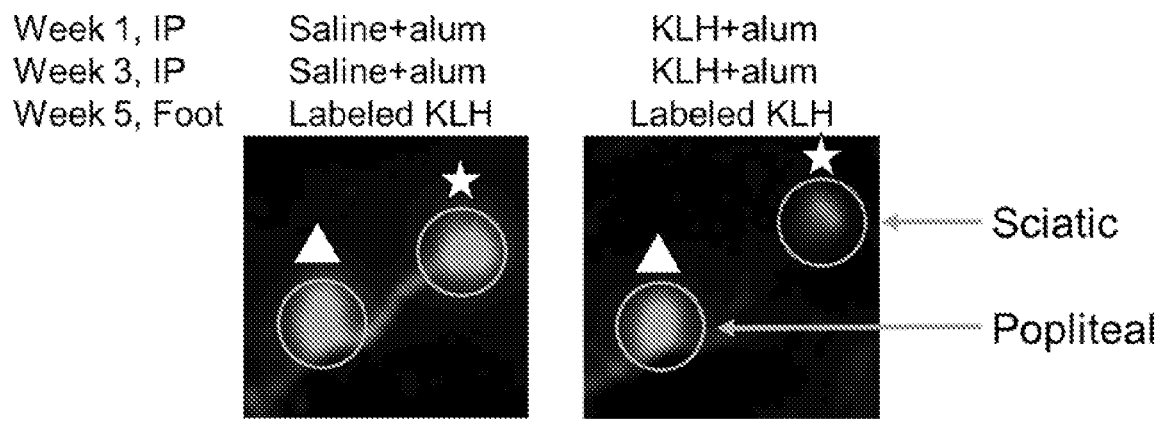
FIG. 2A-2D. Antigen flow is restricted in mice immunized to the injected antigen. A-B) Mice were immunized biweekly with intraperitoneal injections of KLH and alum or saline and alum. Two weeks after the second injection, 200 µg of KLH-800CW was injected into the subcutaneous dorsum of the foot. When the whole mouse was imaged after one hour (A), a lower antigen signal was observed in the sciatic lymph node of KLH-immunized mice compared to naïve mice (B) (naïve, 54.34±8.840, n=5 versus KLH-immunized, 9.730±3.715, n=5, p<0.001 by t-test). A) Images are representative; triangles indicate popliteal lymph nodes while stars mark sciatic lymph nodes. B) Data shown are individual values, plus mean and SEM. C) This effect was specific to the immunized antigen, as OVA signal injected in a mouse immunized to KLH was not reduced at the sciatic lymph node, but OVA injected into OVA-immunized mice was reduced. Images are representative of five animals per group. D) Antigen signal in the sciatic lymph node remained lower in mice injected in the foot for at least 17 weeks after booster injection. Data represent means±SEM. Dotted line indicates average naïve mouse antigen signal. n=5 to 8.
Figure 2B:
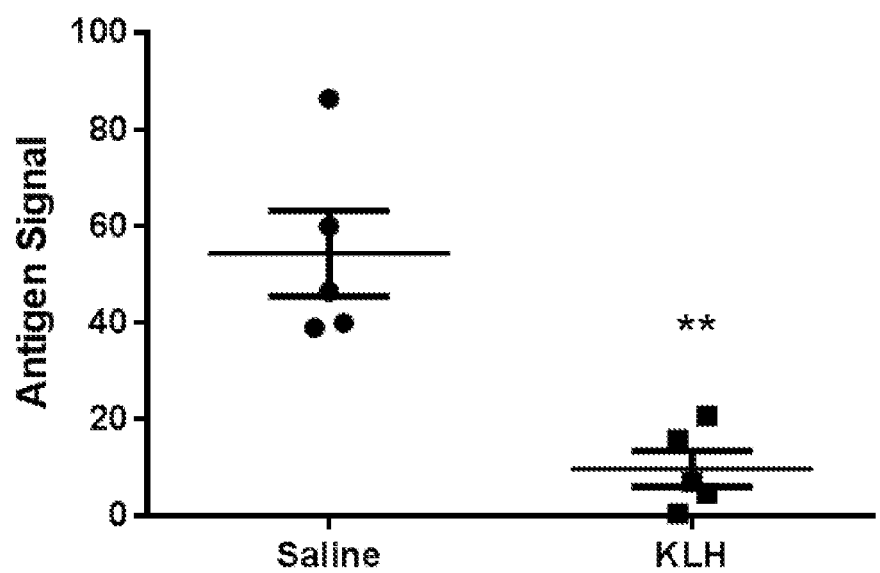

Antigen flow through peripheral lymph nodes is restricted in immunized animals. To determine the effects of vaccination on antigen trafficking, unlabeled antigen with alum as an adjuvant was injected intraperitoneally into mice, twice, two weeks apart. Two weeks after the second injection, KLH-800CW was injected subcutaneously into the dorsum of the hind paw. In cases wherein the mouse had been previously immunized to the antigen, flow of that antigen was restricted; the fluorescent signal trended towards reduced in the popliteal lymph node and was significantly reduced in the sciatic lymph node (naïve, 54.34±8.840, n=5 versus KLH-immunized, 9.730±3.715, n=5, p<0.001 by t-test) (FIG. 2A-B). This indicates a restriction of antigen flow through the lymphatic system.

Figure 2C:
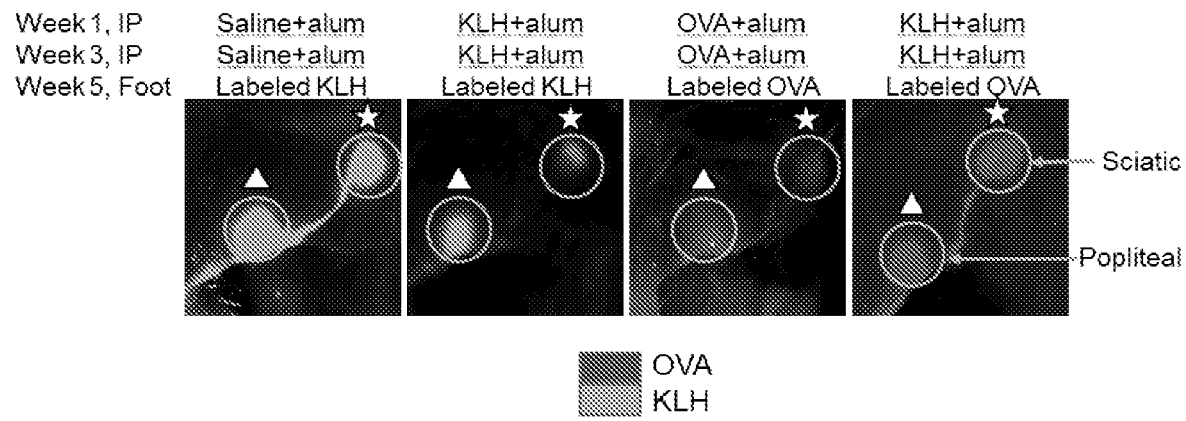
Figure 2D:
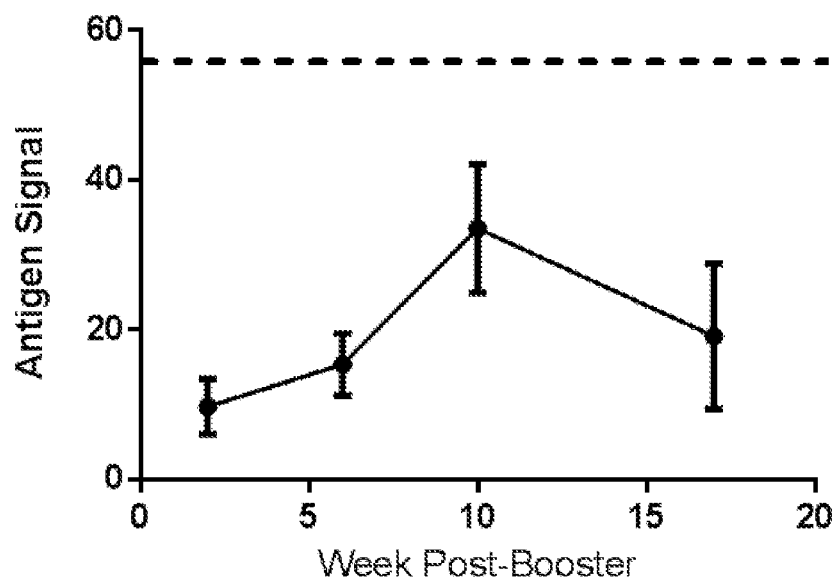

To assess specificity of this restriction, mice immunized with KLH were injected with OVA-680 LT in the hind paw. In animals immunized against KLH, movement of OVA through the lymphatic system was not restricted (FIG. 2C, third panel, OVA), but immunization with OVA led to subsequent restriction of OVA (FIG. 2C, fourth panel, OVA). Therefore, an antigen-specific "memory" leads to subsequent restriction of movement of the same antigen through the draining lymphatics. To determine the durability of the "memory," mice were injected with labeled antigen at various time points after the booster injection, up to 17 weeks later. The amount of antigen in the sciatic lymph node stayed lower in immunized animals for at least 17 weeks after booster (FIG. 2D).

Figure 3A:
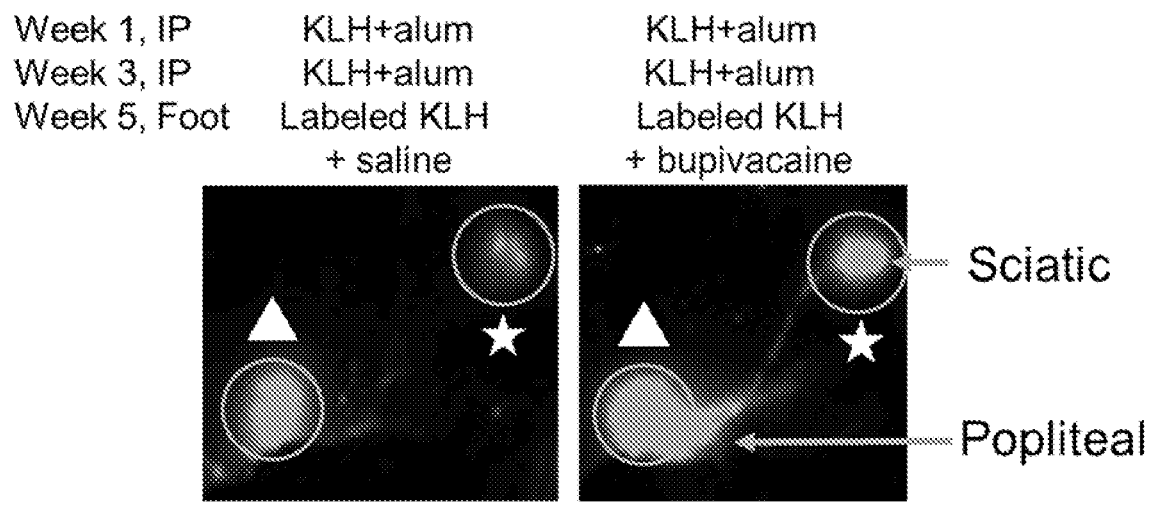
FIG. 3A-3G. Antigen flow restriction is dependent on neural input. A-B) Mice immunized with KLH were injected with bupivacaine at the femoral and sciatic nerves immediately prior to introduction of KLH-800CW (as described in Example 1). When mice were imaged (A), an increase in antigen signal was seen in (B) in the sciatic lymph nodes of mice administered a nerve block (saline, 31.45±3.759, n=10, and bupivacaine, 45.65±5.350, n=9, p<0.05 by t-test). A) Images are representative; triangles indicate popliteal lymph nodes while stars represent sciatic lymph nodes. B) Data shown are individual values. C-D) $Na_V1.8$-DTA mice were immunized with KLH. When compared to littermate controls (C), higher levels of KLH-800CW were found in the sciatic lymph nodes (D) (control, 15.41±3.526, n=13 and $Na_V1.8$-DTA, 35.56±6.035, n=16, p<0.05 by t-test). C) Images are representative; triangles indicate popliteal lymph nodes while stars represent sciatic lymph nodes. D) Data shown are individual values. E-F) Immunized TRPV1-DTA, $Na_V1.8$-DTA and littermate control mice were injected with KLH-800CW in the hind paw as described in Example 1. G) The increase in antigen seen in $Na_V1.8$-DTA mice was not recapitulated in TRPV1-DTA mice in the sciatic lymph node (control, 6.783±1.290, n=9; TRPV1-DTA, 6.345±1.547, n=10, and $Na_V1.8$-DTA, 43.93±15.57, n=6, p<0.001 by one-way ANOVA Bonferroni post-test). Data represent individual values and means±SEM.
Figure 3B:
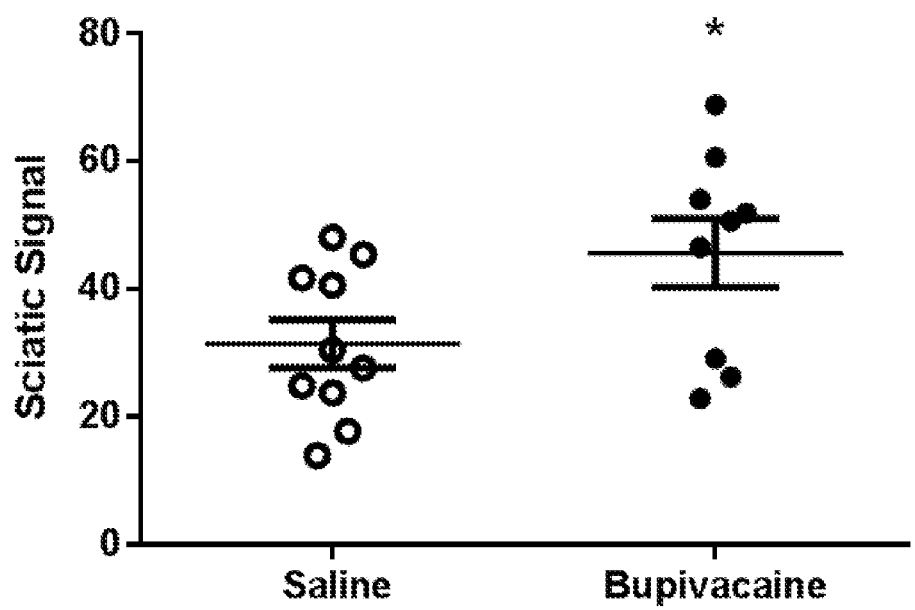

Antigen flow restriction is dependent on sensory neural input. To investigate the involvement of neuronal input on the restriction of movement of antigen through the draining lymphatics, neuronal activation was blocked using bupivacaine, a sodium channel blocker that inhibits afferent neural signals. Animals were immunized with intraperitoneal injections of KLH with 50% alum twice, two weeks apart. Two weeks after the second injection, bupivacaine was injected at the sciatic and femoral nerves, the main bundles innervating the leg. In control animals, the same volume of saline was injected at each location. Blocking of the nerves in immunized mice was sufficient to increase antigen signal in the sciatic lymph node (FIGS. 3A-B) (saline, 31.45±3.759, n=10, and bupivacaine, 45.65±5.350, n=9, p<0.05 by t-test).

Figure 3C:
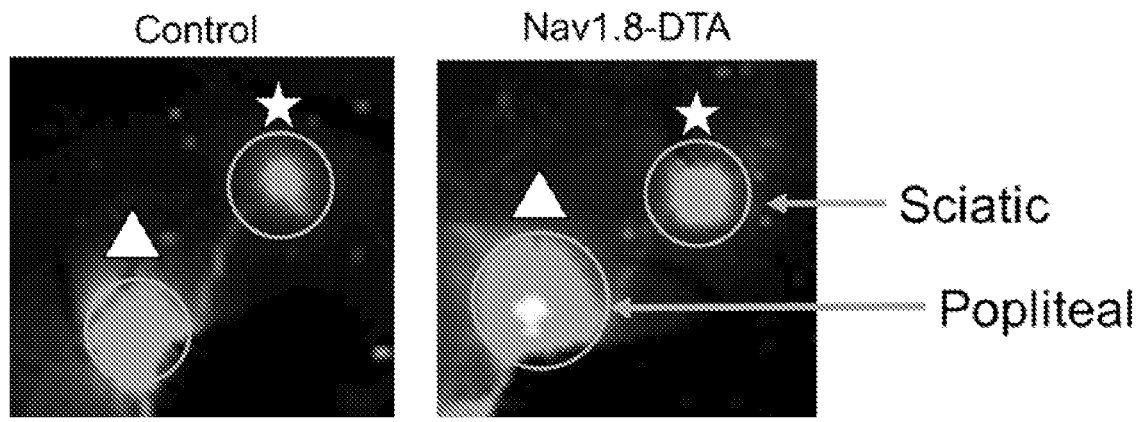
Figure 3D:
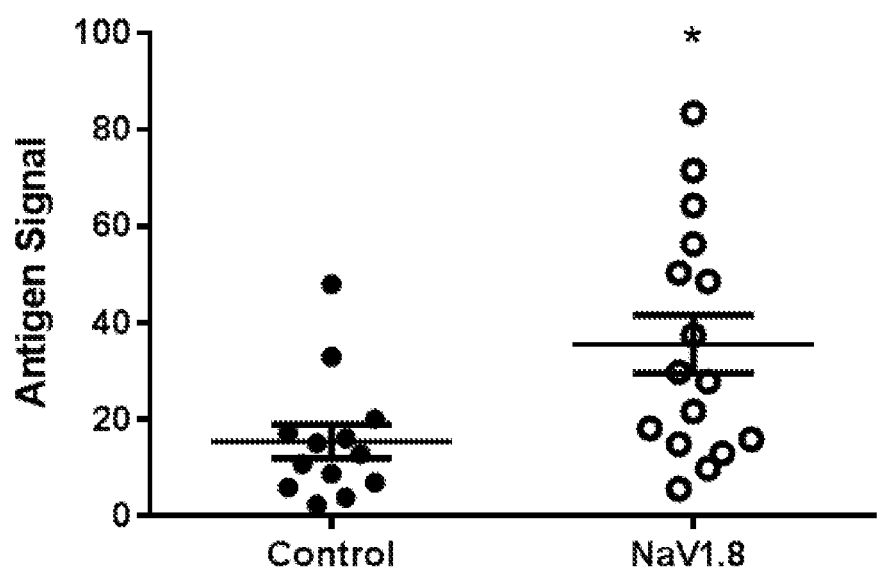
Figure 3E:
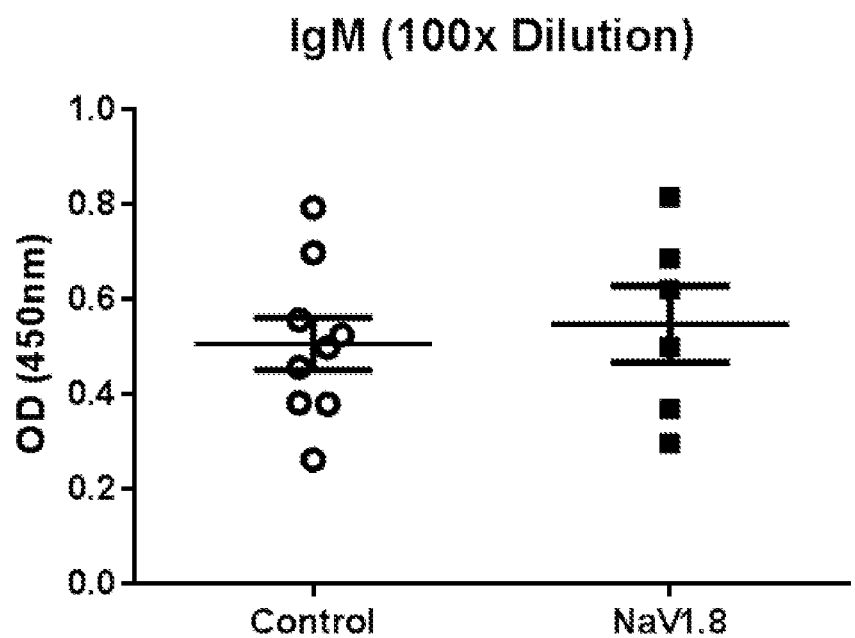
Figure 3F:
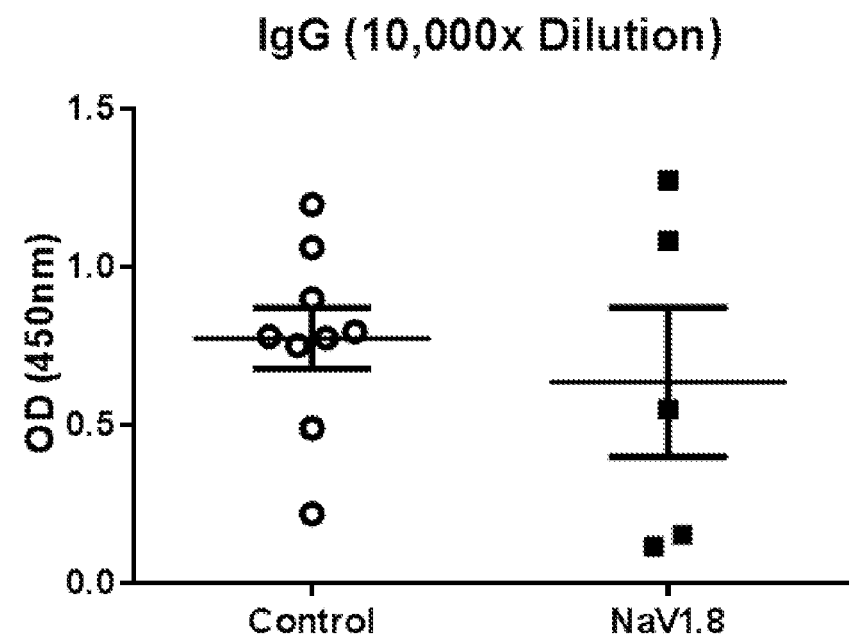

Bupivacaine has a short half-life and may incompletely penetrate the thick sciatic and femoral nerve bundles at the doses given. Therefore, to address the concerns arising from use of a pharmacological agent, and to determine the effect of long-term sensory nerve depletion, a genetically-driven nerve depletion model was used. $Na_V1.8$-expressing nociceptive neurons mediate neurogenic inflammation [42] and neuronal responses to bacterial infections [29]. In the $Na_V1.8$-cre/DTA mouse, $Na_V1.8$-expressing cells also express diphtheria toxin (DTA), effectively ablating the $Na_V1.8$ population [29, 43]. $Na_V1.8$-Cre/DTA and littermate controls were immunized with KLH as described above, and when KLH-800CW was injected into the dorsum of the hind paw, markedly increased amounts of antigen were observed in the sciatic lymph nodes of $Na_V1.8$-Cre/DTA mice compared to littermate control mice (FIG. 3C-D) (control, 15.41±3.526, n=13 versus $Na_V1.8$-DTA, 35.56±6.035, n=16, p<0.05 by t-test). No difference was observed in naïve (non-immunized) $Na_V1.8$-DTA mice, compared to littermate controls (data not shown). Additionally, serum IgG levels against KLH were similar in immunized $Na_V1.8$ and control mice, suggesting that these animals were not merely immunocompromised (FIGS. 3E and 3F). These data suggest that neuronal input is required for the observed restriction of flow of previously immunized antigens through the draining lymphatics.

Figure 3G:
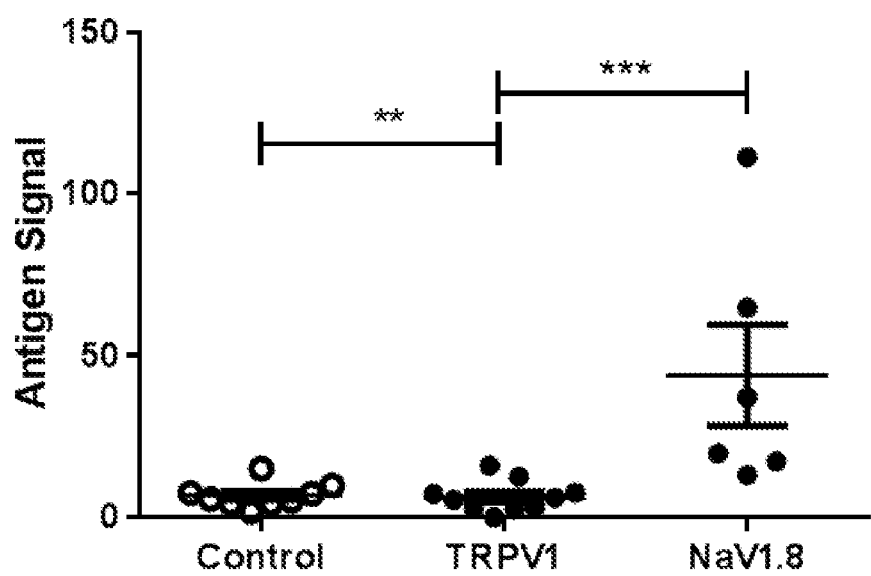

A subset of $Na_V1.8$-expressing nociceptive neurons also express transient receptor potential channel vanilloid 1 (TRPV1), which mediates the pain and sensations associated with capsaicin and heat. These capsaicin-sensitive neurons have been implicated in neuronal responses to infectious bacteria [29]. To determine the contribution of TRPV1-expressing neurons to immunized-antigen lymphatic flow restriction, these neurons were depleted by generating mice that express DTA in TRPV1+ neurons. These mice were immunized with KLH and alum as described above, then KLH-800CW was injected in the dorsum of the hind paw, then imaged after one hour. $Na_V1.8$-DTA and littermate controls were also included as controls. The increase in antigen seen in $Na_V1.8$-DTA mice was not recapitulated in TRPV1-DTA mice in the sciatic lymph node (FIG. 3G) (control, 6.783±1.290, n=9; TRPV1-DTA, 6.345±1.547, n=10; and $Na_V1.8$-DTA, 43.93±15.57, n=6, p<0.001 by one-way ANOVA Bonferroni post-test). This suggests a $TRPV1^{neg}$ $Na_V1.8$+ve population is required for neuronal input leading to restriction of antigen flow through the draining lymphatics.

Figure 4A:
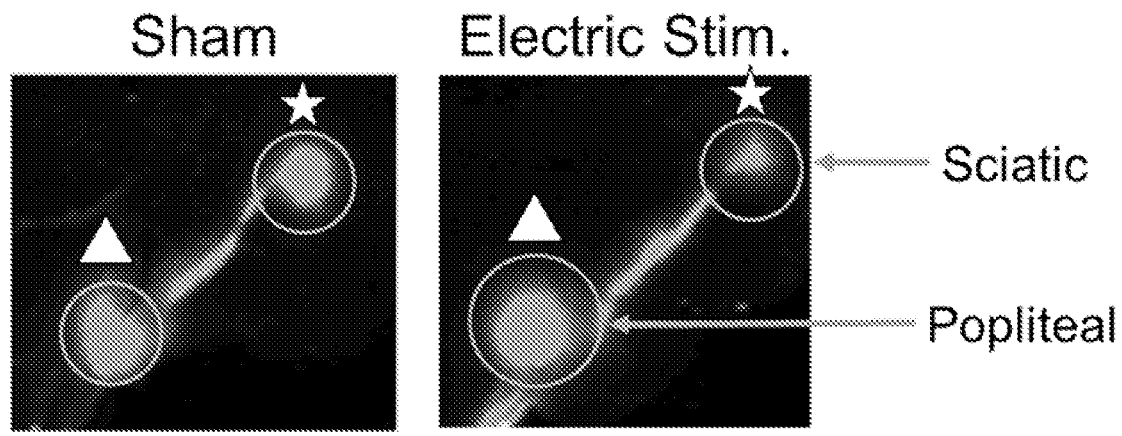
FIG. 4A-4D. Stimulation of neuronal activity initiates reduction antigen flow. A-B) Nerves by the popliteal lymph node were stimulated by application of an electrical current applied through a monopolar needle electrode, followed by injection of KLH-800CW and imaging after one hour. In electrically stimulated animals, lower levels of antigen were observed in the sciatic lymph nodes (sham, 114.1±16.17, n=5 versus electrically stimulated, 56.76±14.38, n=5, p<0.05 by t-test). A) Images are representative. B) Data shown are individual values, together with bars indicating mean and SEM. C-D) A noninvasive magnetic field was applied to the hind leg of naïve mice to induce nerve activity, followed by injection of KLH-800CW. In magnetically stimulated animals, lower levels of antigen were observed in the sciatic lymph nodes (sham, 55.99±4.993, n=10, versus magnetically stimulated, 30.87±4.169, n=12, p<0.001 by t-test). C) Images are representative; triangles indicate popliteal lymph nodes while stars represent sciatic lymph nodes. D) Data shown are individual values, together with bars indicating mean and SEM.
Figure 4B:
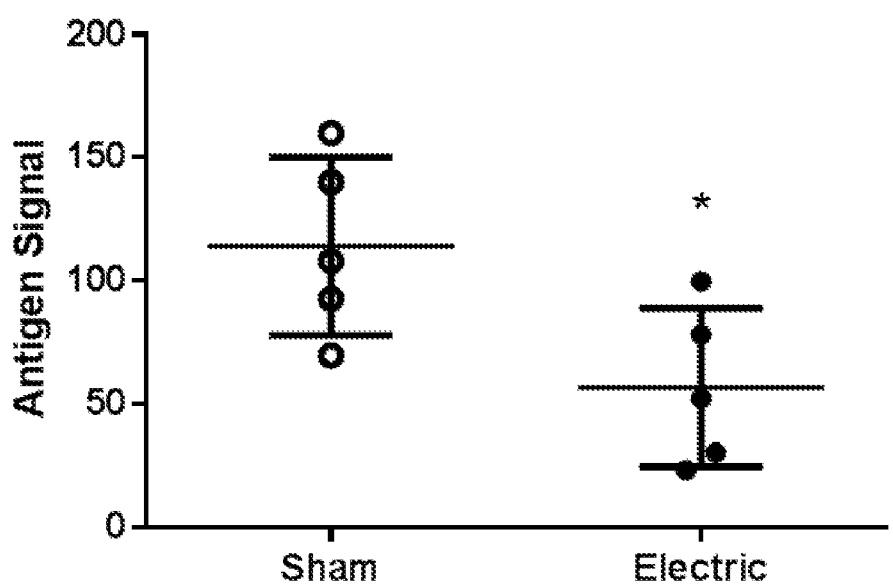

Induction of neuronal activity initiates reduction antigen flow. To determine the role of neurons innervating the lymph nodes in restriction of antigen flow, the femoral and sciatic nerves were electrically stimulated at the popliteal fascia. A monopolar needle electrode was inserted adjacent to the popliteal lymph node of anesthetized animals and electrical current pulses (−5V constant, 0.75 msec pulse duration, 20 Hz) were applied to stimulate the local neurons. In sham animals, a needle electrode and grounding electrode were inserted as above, but no current pulses were applied. After stimulation, KLH-800CW was injected into the dorsum of the hind paw. In electrically stimulated animals, lower levels of antigen were seen in the sciatic lymph nodes (sham, 114.1±16.17, n=5 versus electrically stimulated, 56.76±14.38, n=5, p<0.05 by t-test) (FIGS. 4A-B), indicating that neuronal signals regulate antigen flow through the lymphatic system.

Figure 4C:
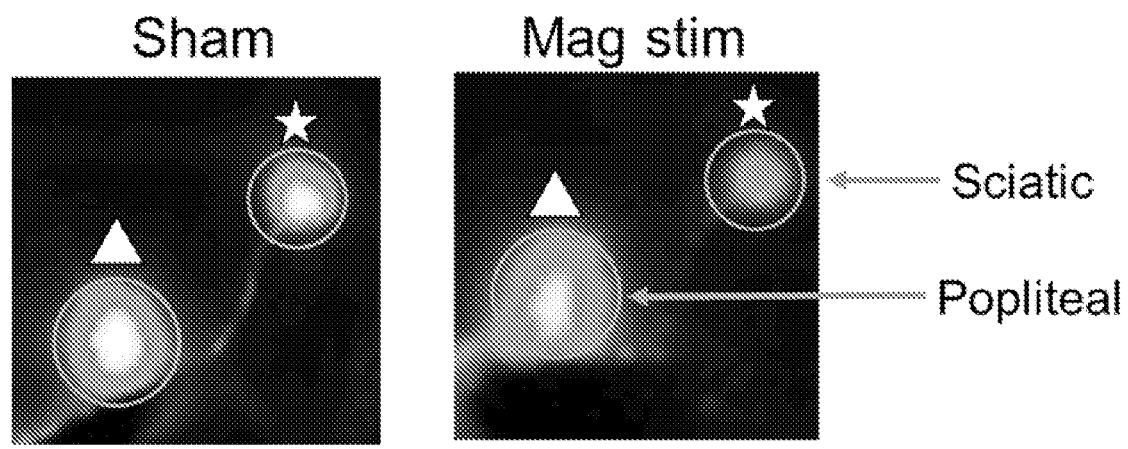
Figure 4D:
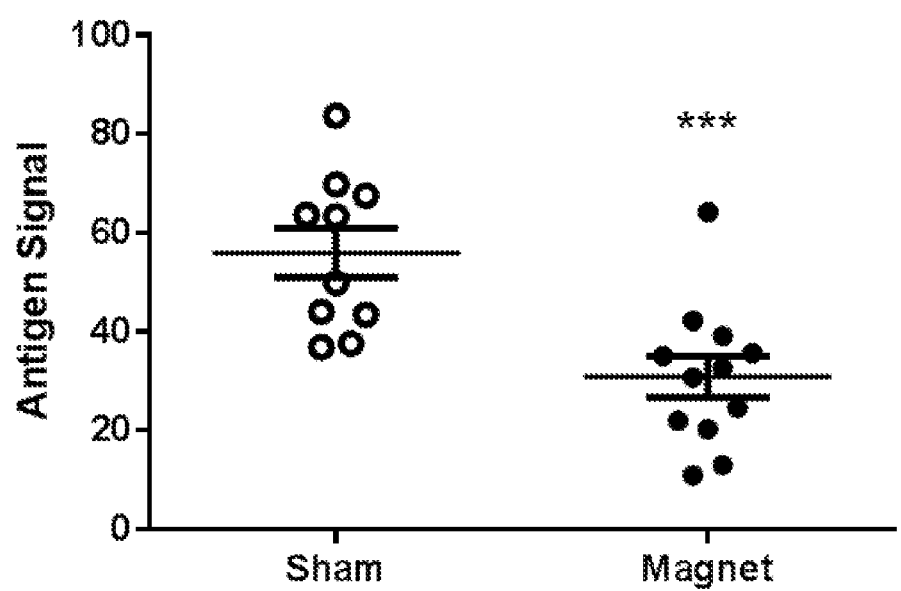

To stimulate the neurons of the leg non-invasively, a time-varying magnetic field was administered with an electromagnetic coil directed to the hind leg of anesthetized naïve mice, followed by injection of KLH-800CW. Sham animals were anesthetized and the coil positioned, but no current applied. In magnetically stimulated animals, lower levels of antigen were seen in the sciatic lymph nodes compared to sham stimulated animals (sham stimulated, 55.99±4.993, n=10, versus magnetically stimulated, 30.87±4.169, n=12, p<0.001 by t-test) (FIGS. 4C-D). Together, these findings indicate that neuronal signals regulate transport of antigens through the lymphatic system.

Figure 5A:
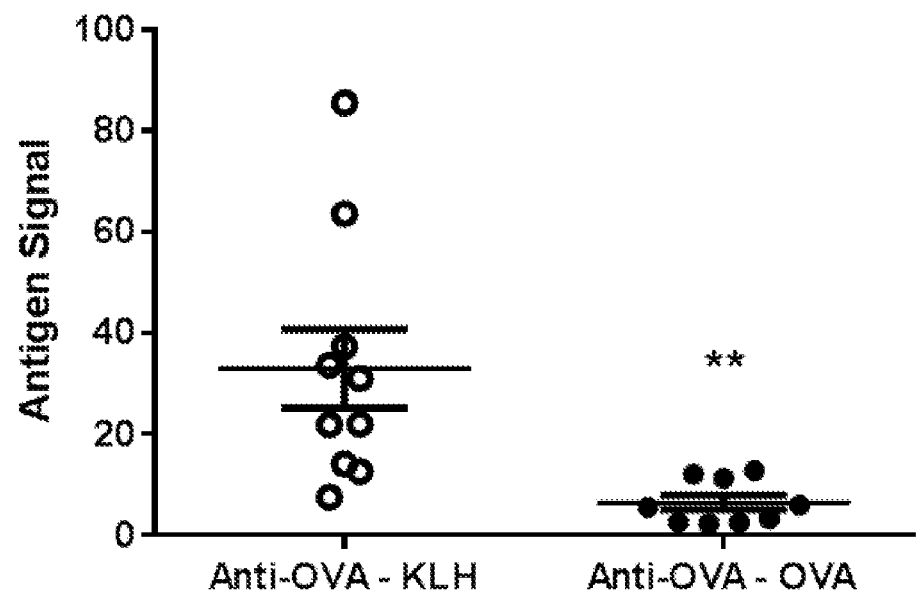
FIG. 5A-5D. Neuronal Fc receptors play a role in antigen restriction. A) Naïve mice were injected intraperitoneally with polyclonal anti-OVA antibodies from rabbit. 24 hours later OVA-800CW or KLH-800CW was injected in the dorsum of the hind paw. The amount of OVA antigen was significantly decreased compared to KLH in the sciatic lymph nodes (KLH, 32.95±7.741, n=10 versus OVA, 6.483±1.461, n=9). B) Immunized Balb/c and FcR KO mice were injected subcutaneously in the hind paw with KLH-800CW. More antigen was seen in the sciatic lymph nodes of FCR KO (Balb/c, 15.76±2.721, n=10 versus FCR KO, 44.29±6.500, n=11, p<0.001 by t-test). D) Mice immunized with KLH were injected with KLH-A647 in the dorsum of the hind paw. After one hour, skin around the injection site was excised, frozen in OCT media and sliced at 10 µm. After mounting tissue slices on slides, they were stained with antibodies against PGP9.5 and FcγRI. Images were obtained on a laser-scanning confocal microscope Images shown are representative of slices from three different animals. White areas in the merged image indicate colocalization of signals from PGP9.5, FcγRI and KLH-A647. Circles indicate regions of interest.

Neuronal Fc receptors play a role in restriction of lymphatic antigen flow. When an animal is immunized against an antigen, one of the responses is production of antibodies specific to this antigen. Because restriction of antigen trafficking in the lymphatic system occurs only when an animal has been immunized against an antigen, we considered that antibody-antigen interactions might underlie the mechanism of restriction. A passive immunization model was utilized to determine whether the presence of antibodies alone would be sufficient to activate restriction of antigen movement. Polyclonal anti-OVA antibodies from rabbit were injected intraperitoneally into naïve mice, and 24 hours later OVA-800CW or KLH-800CW was injected subcutaneous in the dorsum of the hind paw. The accumulation of labeled OVA antigen was significantly decreased compared to the accumulation of labeled KLH antigen in the sciatic lymph nodes (KLH, 32.95±7.741, n=10 versus OVA, 6.483±1.461, n=9) (FIG. 5A).

Figure 5B:
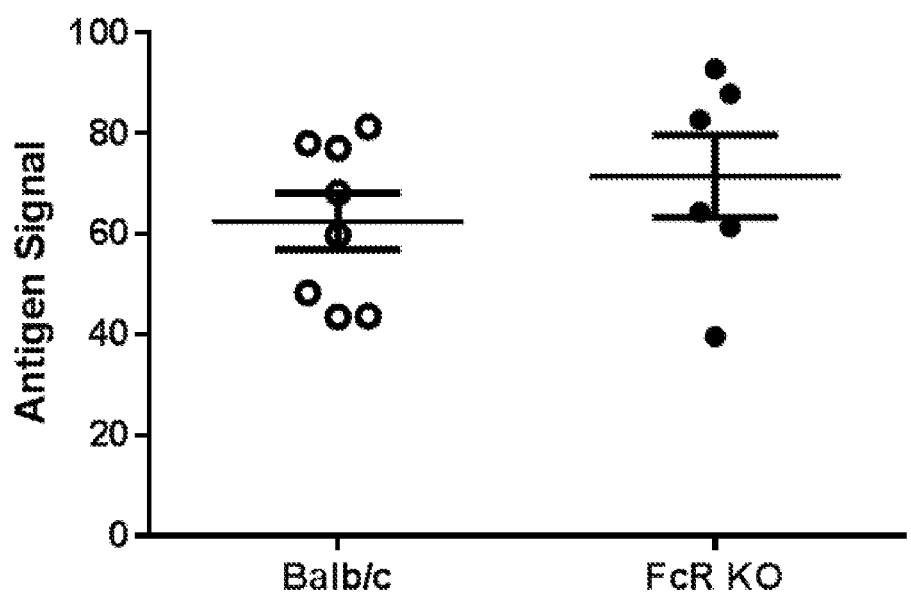
Figure 5C:
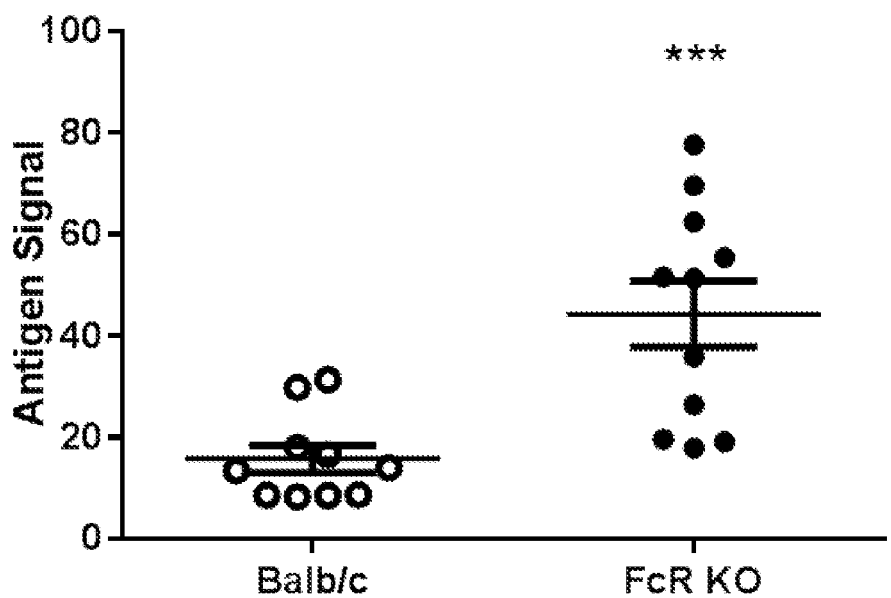
Figure 5D:
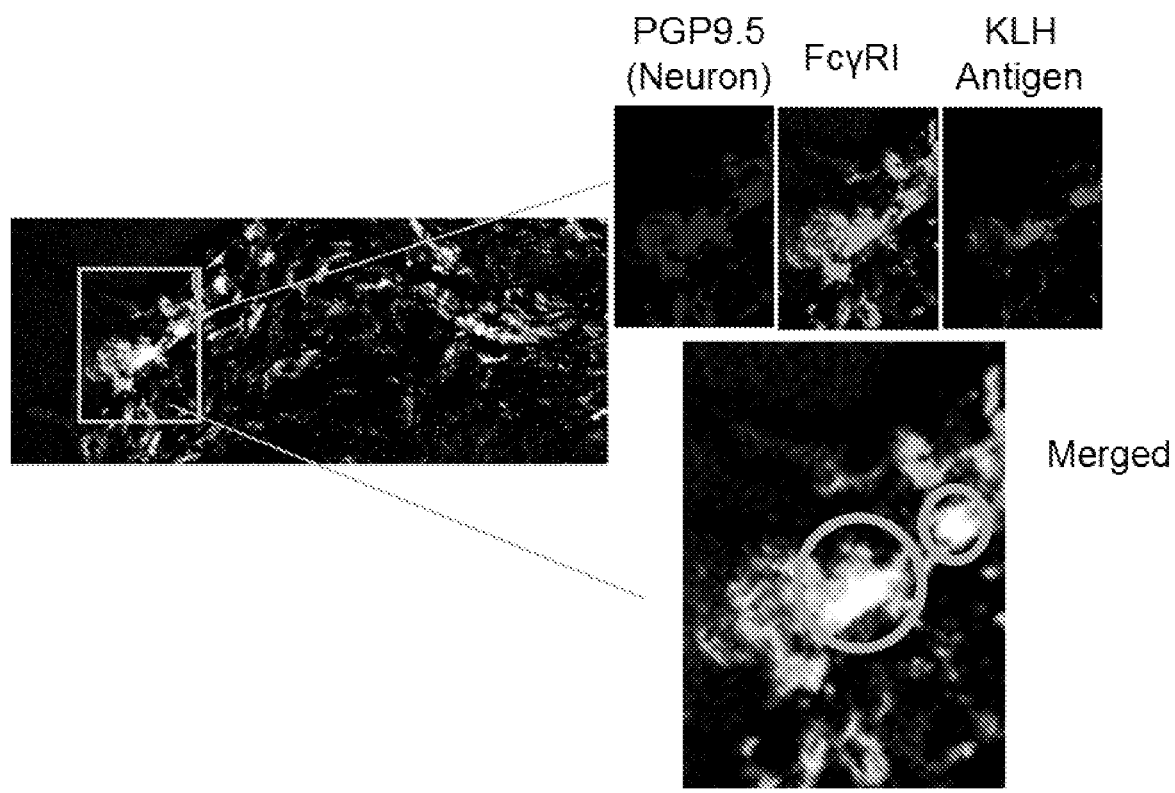

Neuronal Fc receptors are implicated in a mechanism underlying the detection of immunized antigen in the lymphatic system. To determine the role of Fc receptors in restriction of inter-nodal lymphatic translation of antigen in immunized mice, naïve and KLH-immunized Balb/c and FcR KO mice were injected subcutaneously in the hind paw with KLH-800CW. No difference was seen in antigen signals of naïve Balb/c and FcR KO mice in the sciatic lymph node (Balb/c, 62.50±5.614, n=8 versus FCR KO, 71.48±8.197, n=6) (FIG. 5B). Antigen accumulation was higher increased in the sciatic lymph nodes of immunized FCR KO mice vs their Balb/c controls (Balb/c, 15.76±2.721, n=10 versus FCR KO, 44.29±6.500, n=11, $p<0.001$ by t-test) (FIG. 5C). Moreover, in mice immunized with KLH, antigen and Fc receptors colocalized on PGP9.5+ve neuronal tissue at the site of injection (FIG. 5D). Together, these data indicate that neuronal Fc receptors are a necessary component for the nerve-signal dependent restriction of movement of previously immunized antigen through the peripheral lymphatic system.

Discussion

Figure 6:
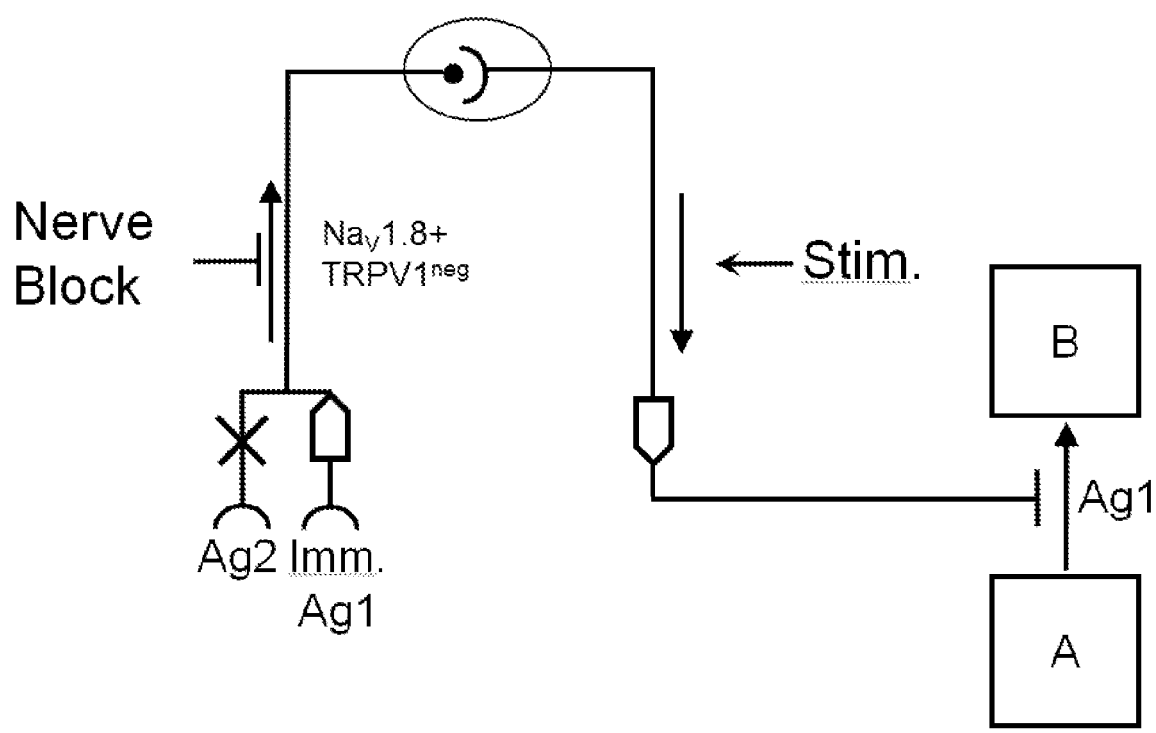
FIG. 6. A model diagram describing the immunized-antigen neuronal response. A neuronal pathway distinguishes between novel and immunized antigens, sending a nerve signal through $Na_V1.8$+ve, $TRPV1^{neg}$ neurons, which is transmuted into a motor signal leading to restriction of antigen flow from lymph node A to lymph node B (e.g., popliteal to sciatic lymph node).

These studies present evidence that neuronal signaling regulates the flow of antigen through peripheral lymph nodes (FIG. 6). In this nerve control circuit, immunized antigen is distinguished from naïve antigen, sending a nerve signal through TRPV1$^{neg}$ Na$_v$1.8+ neurons, which is transformed into a response signal, leading to restriction of antigen flow from lymph node A to lymph node B (e.g., popliteal to sciatic lymph node). The observed restriction of antigen trafficking can be lessened by nerve blockade, inducing the system to treat the immunized antigen as novel. This pathway can be activated by electrically or magnetically stimulating neurons of, for example, the leg, to induce neuronal activity, leading to restriction of novel antigen trafficking through the distal lymph nodes of the stimulated hind quarter.

By extension, this circuit provides a mechanism for the nervous system to rapidly detect invading microorganisms, discern which may be pathogenic, and limit the spread through the lymphatic system by quarantining the offensive organism at the site of invasion. Neurons convey information through temporal patterns of action potentials and graded membrane potential shifts [44-46]. Once bacteria enter the broken skin, they can travel through the lymphatic system, eventually becoming a systemic infection. As small molecules such as KLH and OVA can be stopped in their progression through the lymphatics after neuronal stimulation, it is predictable that movement through the lymphatics of larger antigenic species, such as bacteria and viruses, can also be restricted. In this way, electrical stimulation of the innervating neurons of the draining lymph node soon after a penetrating injury could prevent development of bacteremia and sepsis. Analogously, the movement of cancer cells, especially carcinomas, which metastasize to new locations through the lymphatic system [47-49], might be similarly controlled and restricted. Many therapeutic courses involve lymphatic mapping to determine the lymph nodes draining the site of a primary tumor [50-54]. These lymph nodes are then monitored for development of new micrometastases. The trafficking of these micrometastases can also be halted through neuronal stimulation, halting the spread of secondary tumors. The discovery and characterization of a novel neural circuit wherein sensory and motor nerves regulate antigen trafficking through distal to proximal lymph nodes provides additional insight into the interplay between the nervous and immune systems.

Example 2

Stimulation of Neural Circuits to Lymph Nodes Augments Antigen-Specific Antibody Responses The purpose of this study was to restrict lymphatic transit and augment humoral immunity following antigen immunization by administration of electrical or magnetic stimulation of nerves innervating lymph nodes.

Mice were injected with Keyhole Limpet Hemocyanin (KLH) (20 μg) subcutaneously in the hindpaw. Lower extremity lymphatics were stimulated using needle electrodes or magnetic stimulation on day 0. Anti-KLH IgG antibody titer was assayed weekly following immunization and stimulation.

Figure 7:
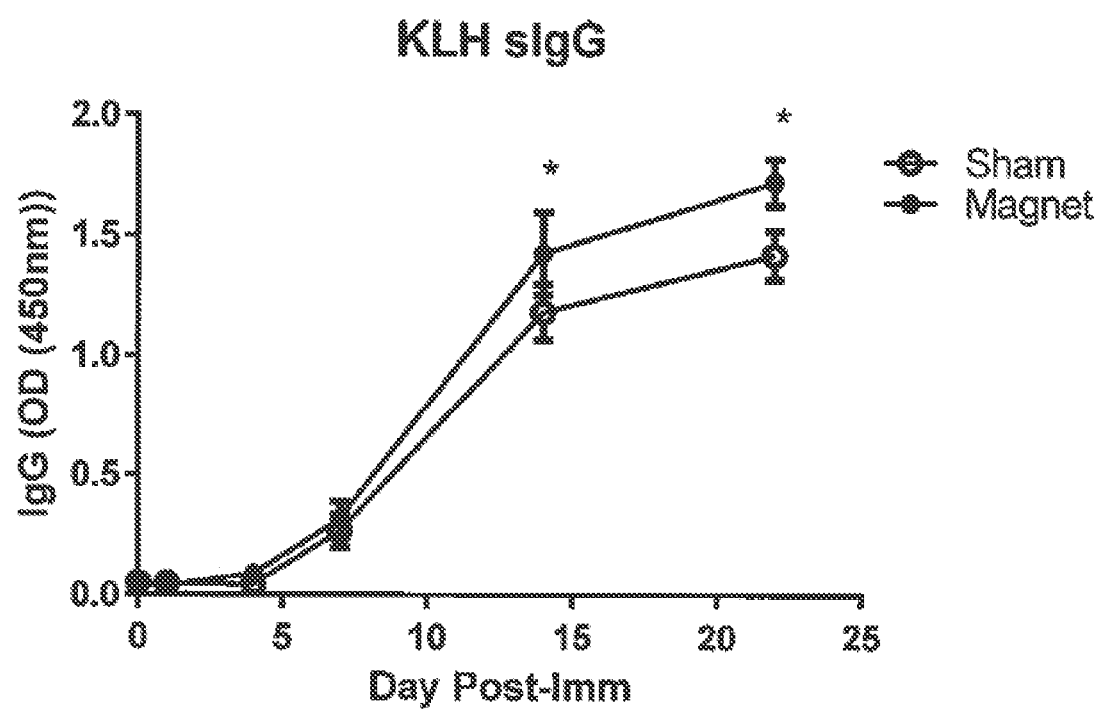
FIG. 7. Induction of neuronal activity by magnetic stimulation increases antibody titers. Balb/c mice were magnetically stimulated or sham stimulated under isoflurane anesthesia. After stimulation, 100 µg KLH and 50% alum in 20 µl were injected in the dorsum of the hind paw. Serum was drawn at days 0, 1, 4, 7, 14 and 22 and analyzed for anti-KLH IgG antibodies by ELISA.
Figure 8:
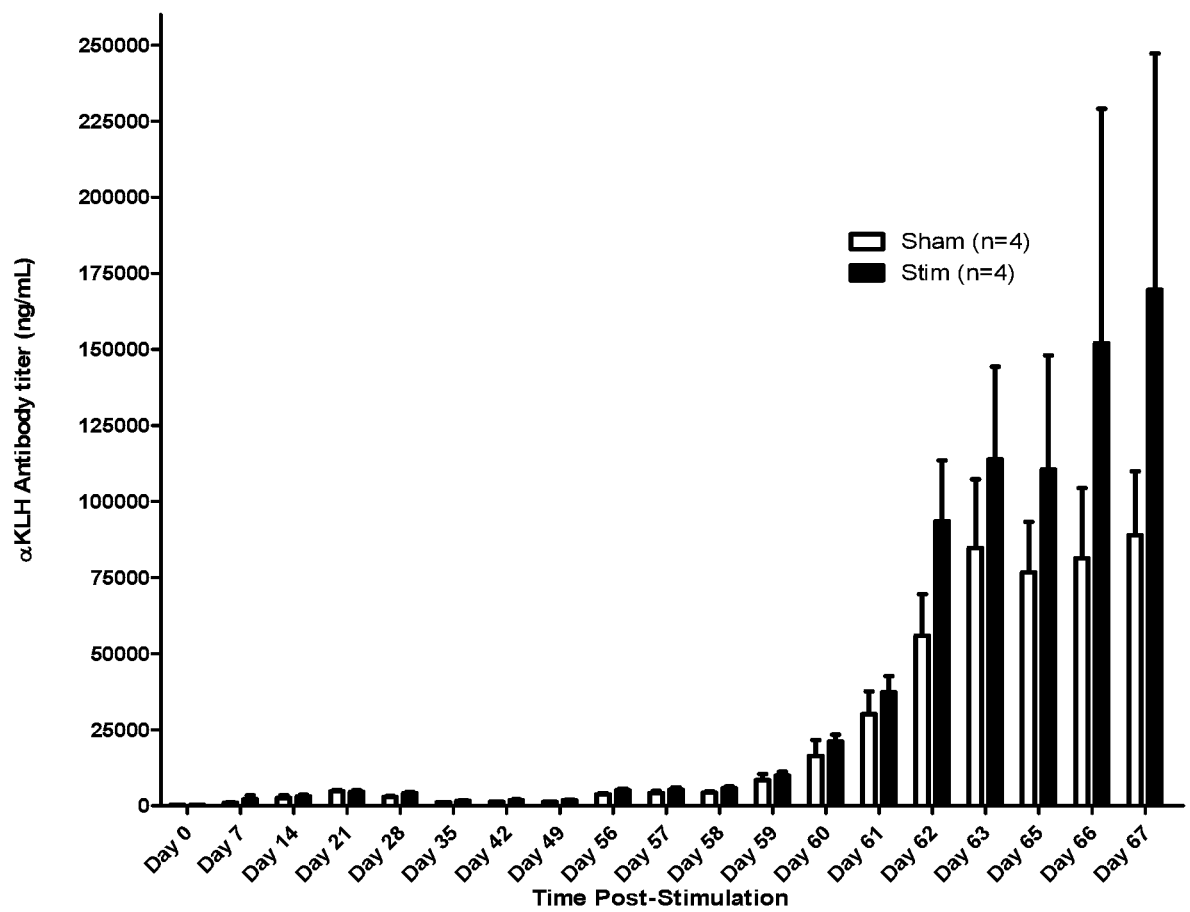
FIG. 8. A single electrical stimulation of the neural circuits to lymph nodes augments antigen-specific antibody responses. αKLH IgG titer following KLH immunization and electrical stimulation with subsequent KLH challenge. One-time electronic stimulation and KLH (20 µg) immunization were applied on Day 0. A subsequent KLH (2 µg) challenge was applied on Day 56.
Figure 9:
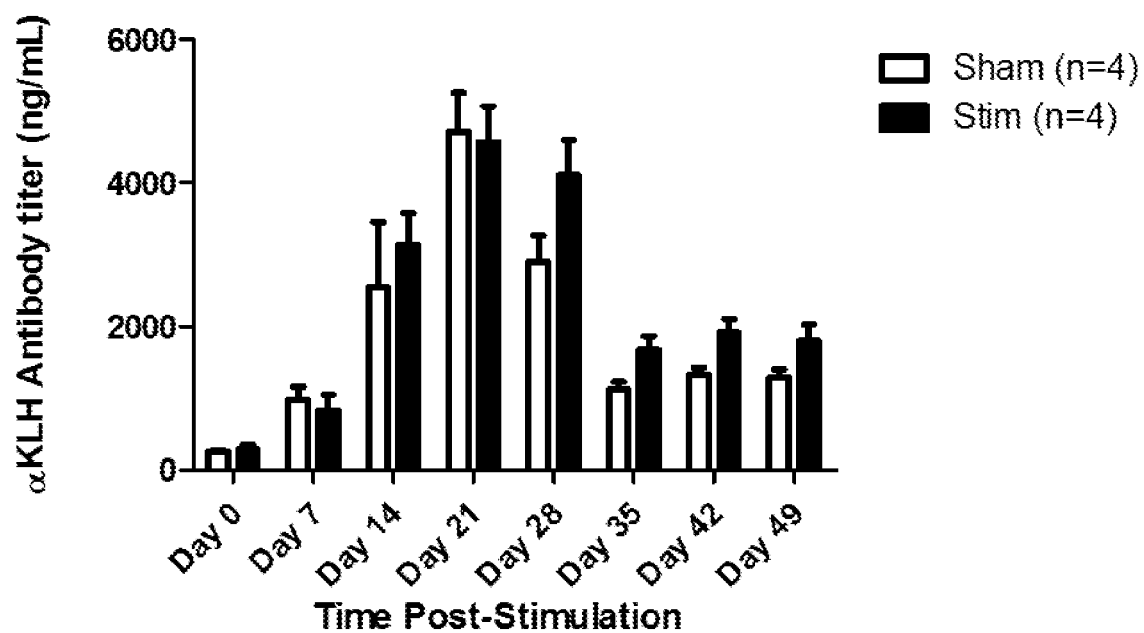
FIG. 9. A single electrical stimulation of the neural circuits to lymph nodes augments antigen-specific antibody responses. αKLH IgG titer following KLH (20 µg) immunization and electrical stimulation applied on Day 0.

A single electric or magnetic stimulation of the neural circuits to the lymph nodes augmented the ensuing antigen-specific antibody responses (FIGS. 7-9).

REFERENCES

1. Itano, A. A., et al., *Distinct dendritic cell populations sequentially present antigen to CD4 T cells and stimulate different aspects of cell-mediated immunity*. Immunity, 2003. 19(1): p. 47-57.
2. Sixt, M., et al., *The conduit system transports soluble antigens from the afferent lymph to resident dendritic cells in the T cell area of the lymph node*. Immunity, 2005. 22(1): p. 19-29.
3. Moe, R. E., *Electron Microscopic Appearance of the Parenchyma of Lymph Nodes*. Am J Anat, 1964. 114(2): p. 341-69.
4. Roozendaal, R., et al., *Conduits mediate transport of low-molecular-weight antigen to lymph node follicles*. Immunity, 2009. 30(2): p. 264-76.
5. Inaba, K., et al., *Efficient presentation of phagocytosed cellular fragments on the major histocompatibility complex class II products of dendritic cells*. J Exp Med, 1998. 188(11): p. 2163-73.
6. Manickasingham, S. and C. Reis e Sousa, *Microbial and T cell-derived stimuli regulate antigen presentation by dendritic cells in vivo*. J Immunol, 2000. 165(9): p. 5027-34.
7. Germain, R. N., *MHC-dependent antigen processing and peptide presentation: providing ligands for T lymphocyte activation*. Cell, 1994. 76(2): p. 287-99.
8. Rajewsky, K., *Clonal selection and learning in the antibody system*. Nature, 1996. 381(6585): p. 751-8.
9. Nossal, G. J. V., et al., *Antigens in immunity: VIII. Localization of (125)I-labelled antigens in the secondary response*. Immunology, 1965. 9(4): p. 349-357.

10. Ada, G. L. and P. G. Lang, *Antigen in tissues: II. State of antigen in lymph node of rats given isotopically-labelled flagellin, haemocyanin or serum albumin*. Immunology, 1966. 10(5): p. 431-443.

11. Lang, P. G. and G. Ada, *Antigen in tissues: IV. The effect of antibody on the retention and localization of antigen in rat lymph nodes\**. Immunology, 1967. 13(5): p. 523.

12. Shepherd, A. J., J. E. G. Downing, and J. A. Miyan, *Without nerves, immunology remains incomplete—in vivo veritas*. Immunology, 2005. 116(2): p. 145-163.

13. Tonkoff, W., *Zur Kenntnis der Nerven der Lymphdrüsen*. Anat Anz, 1899. 16: p. 456-459.

14. Felten, D. L., et al., *Sympathetic innervation of lymph nodes in mice*. Brain research bulletin, 1984. 13(6): p. 693-699.

15. Felten, D., et al., *Noradrenergic and peptidergic innervation of lymphoid tissue*. Journal of immunology (Baltimore, Md.: 1950), 1985. 135(2 Suppl): p. 755s-765s.

16. Novotny, G. and K. Kliche, *Innervation of lymph nodes: A combined silver impregnation and electron-microscopic study*. Cells Tissues Organs, 1986. 127(4): p. 243-248.

17. Villaro, A., M. Sesma, and J. Vazquez, *Innervation of mouse lymph nodes: Nerve endings on muscular vessels and reticular cells*. American journal of anatomy, 1987. 179(2): p. 175-185.

18. Fink, T. and E. Weihe, *Multiple neuropeptides in nerves supplying mammalian lymph nodes: messenger candidates for sensory and autonomic neuroimmunomodulation?* Neuroscience letters, 1988. 90(1): p. 39-44.

19. Andersson, U. and K. J. Tracey, *Neural reflexes in inflammation and immunity*. J Exp Med, 2012. 209(6): p. 1057-68.

20. Borovikova, L. V., et al., *Vagus nerve stimulation attenuates the systemic inflammatory response to endotoxin*. Nature, 2000. 405(6785): p. 458-462.

21. Elenkov, I. J., et al., *The sympathetic nerve—an integrative interface between two supersystems: the brain and the immune system*. Pharmacological reviews, 2000. 52(4): p. 595-638.

22. Feldman, R. D., G. Hunninghake, and W. McArdle, *Beta-adrenergic-receptor-mediated suppression of interleukin 2 receptors in human lymphocytes*. The Journal of Immunology, 1987. 139(10): p. 3355-3359.

23. Elenkov, I. J., et al., *Modulation of lipopolysaccharide-induced tumor necrosis factor-α production by selective α-and β-adrenergic drugs in mice*. Journal of neuroimmunology, 1995. 61(2): p. 123-131.

24. Benschop, R. J., et al., *Adrenergic control of natural killer cell circulation and adhesion*. Brain, behavior, and immunity, 1997. 11(4): p. 321-332.

25. Sanders, V. M., et al., *Differential expression of the beta2-adrenergic receptor by Th1 and Th2 clones: implications for cytokine production and B cell help*. The Journal of Immunology, 1997. 158(9): p. 4200-4210.

26. Mina-Osorio, P., et al., *Neural signaling in the spleen controls B-cell responses to blood-borne antigen*. Molecular medicine, 2012. 18(1): p. 618-27.

27. Nakai, A., et al., *Control of lymphocyte egress from lymph nodes through β2-adrenergic receptors*. The Journal of experimental medicine, 2014. 211(13): p. 2583-2598.

28. Sun, J., et al., *Neuronal GPCR Controls Innate Immunity by Regulating Noncanonical Unfolded Protein Response Genes*. Science, 2011. 332(6030): p. 729-732.

29. Chiu, I. M., et al., *Bacteria activate sensory neurons that modulate pain and inflammation*. Nature, 2013. 501(7465): p. 52-57.

30. Andoh, T. and Y. Kuraishi, *Direct action of immunoglobulin G on primary sensory neurons through Fc gamma receptor*. The FASEB Journal, 2003.

31. Andoh, T. and Y. Kuraishi, *Expression of Fc epsilon receptor I on primary sensory neurons in mice*. Neuroreport, 2004. 15(13): p. 2029-31.

32. van der Kleij, H., et al., *Evidence for neuronal expression of functional Fc (ε and γ) receptors*. Journal of Allergy and Clinical Immunology, 2010. 125(3): p. 757-760.

33. Qu, L., *Neuronal Fc gamma receptor I as a novel mediator for IgG immune complex-induced peripheral sensitization*. Neural Regeneration Research, 2012. 7(26): p. 2075-2079.

34. von Andrian, U. H. and T. R. Mempel, *Homing and cellular traffic in lymph nodes*. Nat Rev Immunol, 2003. 3(11): p. 867-878.

35. Junt, T., et al., *Subcapsular sinus macrophages in lymph nodes clear lymph-borne viruses and present them to antiviral B cells*. Nature, 2007. 450(7166): p. 110-4.

36. Phan, T. G., et al., *Subcapsular encounter and complement-dependent transport of immune complexes by lymph node B cells*. Nat Immunol, 2007. 8(9): p. 992-1000.

37. Carrasco, Y. R. and F. D. Batista, *B cells acquire particulate antigen in a macrophage-rich area at the boundary between the follicle and the subcapsular sinus of the lymph node*. Immunity, 2007. 27(1): p. 160-71.

38. Roozendaal, R., et al., *Conduits mediate transport of low-molecular-weight antigen to lymph node follicles*. Immunity, 2009. 30(2): p. 264-276.

39. Iannacone, M., et al., *Subcapsular sinus macrophages prevent CNS invasion on peripheral infection with a neurotropic virus*. Nature, 2010. 465(7301): p. 1079-83.

40. Agarwal, N., S. Offermanns, and R. Kuner, *Conditional gene deletion in primary nociceptive neurons of trigeminal ganglia and dorsal root ganglia*. Genesis, 2004. 38(3): p. 122-9.

41. Barthold, S. W., K. Bayne, and M. Davis, *Guide for the care and use of laboratory animals*. 2011, Washington: National Academy Press.

42. Chiu, I. M., C. A. von Hehn, and C. J. Woolf, *Neurogenic inflammation and the peripheral nervous system in host defense and immunopathology*. Nat Neurosci, 2012. 15(8): p. 1063-7.

43. Abrahamsen, B., et al., *The cell and molecular basis of mechanical, cold, and inflammatory pain*. Science, 2008. 321(5889): p. 702-5.

44. Bialek, W., et al., *Reading a neural code*. Science, 1991. 252: p. 1854+.

45. Borst, A. and F. E. Theunissen, *Information theory and neural coding*. Nat Neurosci, 1999. 2(11): p. 947-957.

46. Stanley, G. B., *Reading and writing the neural code*. Nature Neuroscience, 2013. 16(3): p. 259-263.

47. Cochran, A. J., D.-R. Wen, and D. L. Morton, *Management of the regional lymph nodes in patients with cutaneous malignant melanoma*. World journal of surgery, 1992. 16(2): p. 214-221.

48. Fidler, I. J., *The pathogenesis of cancer metastasis: the 'seed and soil' hypothesis revisited*. Nature Reviews Cancer, 2003. 3(6): p. 453-458.

49. Shayan, R., M. G. Achen, and S. A. Stacker, *Lymphatic vessels in cancer metastasis: bridging the gaps*. Carcinogenesis, 2006. 27(9): p. 1729-1738.

50. Morton, D. L., et al., *Technical details of intraoperative lymphatic mapping for early stage melanoma*. Archives of surgery, 1992. 127(4): p. 392-399.

51. Bilchik, A. J., et al., *Universal application of intraoperative lymphatic mapping and sentinel lymphadenectomy in solid neoplasms*. The Cancer Journal, 1998. 4(6): p. 351.
52. Nieweg, O. E., P. J. Tanis, and B. B. Kroon, *The definition of a sentinel node*. Annals of Surgical Oncology, 2001. 8(6): p. 538-541.
53. Ferris, R. L., et al., *Molecular staging of cervical lymph nodes in squamous cell carcinoma of the head and neck*. Cancer research, 2005. 65(6): p. 2147-2156.
54. Park, C., et al., *Internal mammary sentinel lymph node mapping for invasive breast cancer: implications for staging and treatment*. The breast journal, 2005. 11(1): p. 29-33.

What is claimed is:

1. A method of inhibiting systemic infection by infectious pathogens in a subject, the method comprising electrical and/or magnetic stimulation of one or more peripheral nerves innervating one or more lymph nodes draining a site of infection in the subject to constrain the infectious pathogens from traveling through the subject's lymphatic system, wherein unconstrained travel of the infectious pathogens through the subject's lymphatic system leads to systemic infection, thereby inhibiting systemic infection by the infectious pathogens in the subject;
wherein the electrical stimulation of the one or more peripheral nerves comprises a train of 0.75 msec duration pulses applied at 2-20 Hz, or wherein the magnetic stimulation of the one or more peripheral nerves comprises a train of pulses applied at 2 Hz using an electromagnetic coil that creates a time-variable magnetic field.

2. The method of claim 1, wherein the stimulation is applied after a penetrating injury to the subject's skin.

3. The method of claim 1, wherein the infectious pathogens are bacteria.

4. The method of claim 1, wherein the one or more peripheral nerves innervating the one or more lymph nodes drain a site of a penetrating injury to the subject's skin and stimulation of the one or more peripheral nerves innervating the one or more lymph nodes inhibits bacteremia and sepsis.

5. The method of claim 1, wherein the stimulation of the one or more peripheral nerves comprises stimulation of femoral and sciatic nerves in the popliteal fascia.

6. The method of claim 1, wherein the stimulation is electrical stimulation applied using a monopolar or bipolar needle electrode, a cluster of penetrating electrodes, percutaneous electrical nerve stimulation (PENS), transcutaneous electrical nerve stimulation (TENS), or a chronically implanted nerve stimulator.

7. The method of claim 1, wherein the stimulation is applied for a duration of at least 1 minute.

8. The method of claim 1, wherein the stimulation is applied in one session.

9. A method of inhibiting formation of metastases in a subject, the method comprising electrical and/or magnetic stimulation of one or more peripheral nerves innervating one or more lymph nodes draining a site of a primary tumor in the subject to restrict tumor cells and micrometastases from traveling through the subject's lymphatic system, wherein unrestricted travel of the tumor cells and micrometastases through the subject's lymphatic system leads to recolonization of cancer cells and formation of a metastatic tumor, thereby inhibiting the formation of metastases in the subject,
wherein the electrical stimulation of the one or more peripheral nerves comprises a train of 0.75 msec duration pulses applied at 2-20 Hz, or wherein the magnetic stimulation of the one or more peripheral nerves comprises a train of pulses applied at 2 Hz using an electromagnetic coil that creates a time-variable magnetic field.

10. The method of claim 9, wherein the stimulation is electrical stimulation applied using a monopolar or bipolar needle electrode, a cluster of penetrating electrodes, percutaneous electrical nerve stimulation (PENS), transcutaneous electrical nerve stimulation (TENS), or a chronically implanted nerve stimulator.

11. A method of providing a vaccine adjuvant in a subject who has received a vaccine, the method comprising electrical and/or magnetic stimulation of one or more peripheral nerves innervating one or more lymph nodes of the subject who has received the vaccine to increase antibody production to an antigen present in the vaccine, thereby providing a vaccine adjuvant in the subject,
wherein the electrical stimulation of the one or more peripheral nerves comprises a train of 0.75 msec duration pulses applied at 2-20 Hz, or wherein the magnetic stimulation of the one or more peripheral nerves comprises a train of pulses applied at 2 Hz using an electromagnetic coil that creates a time-variable magnetic field.

12. The method of claim 11, wherein the stimulation is electrical stimulation applied using a monopolar or bipolar needle electrode, a cluster of penetrating electrodes, percutaneous electrical nerve stimulation (PENS), transcutaneous electrical nerve stimulation (TENS), or a chronically implanted nerve stimulator.

* * * * *